United States Patent
Dickens et al.

(10) Patent No.: US 8,759,519 B2
(45) Date of Patent: Jun. 24, 2014

(54) MONO-HYDROCHLORIC SALTS OF AN INHIBITOR OF HISTONE DEACETYLASE

(75) Inventors: Julius W. J. Dickens, Beerse (BE); Ioannes Nicolaos Houpis, Antwerp (BE); Yolande Lydia Lang, Vosselaar (BE); Carina Leys, Stabroek (BE); Sigrid Carl Maria Stokbroekx, Beerse (BE); Johan Erwin Edmond Weerts, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 26 days.

(21) Appl. No.: 13/483,678

(22) Filed: May 30, 2012

(65) Prior Publication Data

US 2012/0289527 A1   Nov. 15, 2012

Related U.S. Application Data

(62) Division of application No. 12/598,743, filed as application No. PCT/EP2008/055804 on May 13, 2008, now abandoned.

(60) Provisional application No. 60/917,821, filed on May 14, 2007.

(30) Foreign Application Priority Data

May 14, 2007   (EP) .................................. 07108176

(51) Int. Cl.
*C07D 405/14* (2006.01)
*C07D 211/26* (2006.01)

(52) U.S. Cl.
USPC ......................................... 544/331; 546/229

(58) Field of Classification Search
USPC .......................................... 544/331; 546/229
See application file for complete search history.

(56) References Cited

U.S. PATENT DOCUMENTS 4,344,948 A   8/1982   Takai et al.

FOREIGN PATENT DOCUMENTS

| WO | WO 97/21701 | 6/1997 |
|---|---|---|
| WO | WO 2006/010750 | 2/2006 |

OTHER PUBLICATIONS

Adeyeye, M. "Preformulation in Solid Dosage form Development" (2.3 Salt Selection for Pharmaceutical Compounds). Informa Healthcare, (2008), pp. 63-80.
Bastin, R.J. et al. "Salt Selection and Optimisation Procedures for Pharmaceutical New Chemical Entities", Organic Process Research & Development, (2000), vol. 4, pp. 427-435.
Gould, P.L "Salt Selection for Basic Drugs", International Journal of Pharmaceutics, vol. 33, (1986), pp. 201-217.
Liu, R. et al. Water-Insoluble Drug Formulation (CRC Press, 2008), Chapter 15, pp. 417-435.
Morris, K.R. et al. "An Integrated Approach to the Selection of Optimal Salt Form for a New Drug Candidate", International Journal of Pharmaceutics, 105 (1994) pp. 209-217.
Serajuddin, A.T.M., "Salt Formation to Improve Drug Solubility", Advanced Drug Delivery Reviews, 59, (2007), pp. 603-616.
Stahl, P.H. et al., eds., "Handbook of Pharmaceutical Salts. Properties, Selection, and Use", (2008), pp. 265-327.

*Primary Examiner* — Deedpak Rao

(57) ABSTRACT

This invention provides novel crystalline forms of mono-HCl salts and a mono-HCl salt hydrate of JNJ-26481585, an inhibitor of histone deacetylases. The invention also relates to processes for production of these forms, to intermediates used in these processes, to pharmaceutical compositions comprising these forms, and to the use of these forms in medical treatment for instance as a medicine to inhibit proliferative conditions, such as cancer and leukemia.

4 Claims, 16 Drawing Sheets

Infrared spectrometry: Form I

Powder XRD: Form I

DSC: Form I

Powder XRD: Form II

DSC: Form II

Powder XRD: Hydrated form

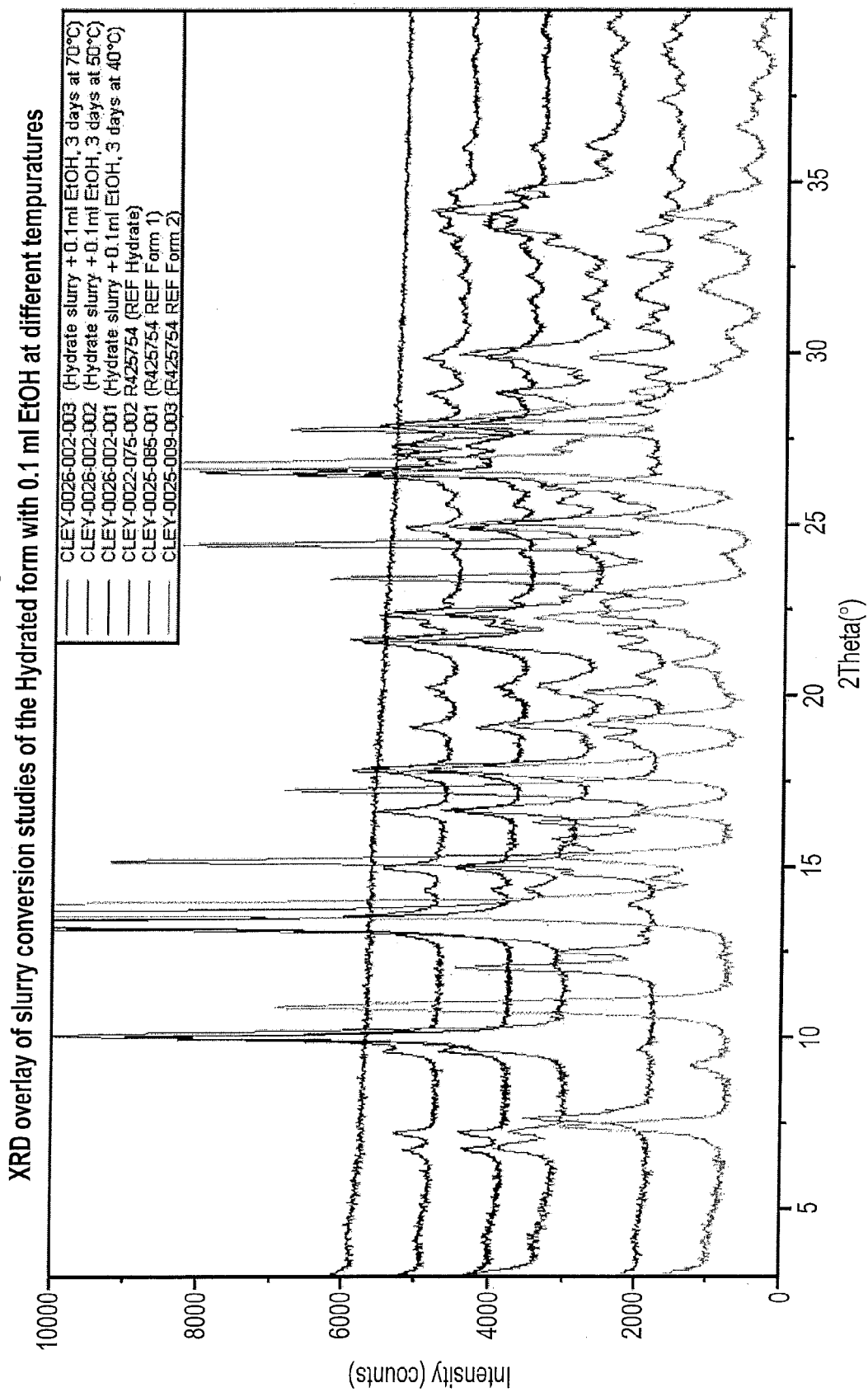

MONO-HYDROCHLORIC SALTS OF AN INHIBITOR OF HISTONE DEACETYLASE

CROSS REFERENCE TO RELATED APPLICATIONS

This application is a Divisional of U.S. application Ser. No. 12/598,743, filed Nov. 3, 2009 now abandoned, which is a U.S. National Stage Filing under 371 of PCT/EP08/055,804 filed May 13, 2008, which application claims priority from EPO Patent Application EP07108176.4 filed May 14, 2007 which claims benefit of U.S. Provisional 60/917,821 filed May 14, 2007, the entire disclosures of which are hereby incorporated in their entirety.

FIELD OF THE INVENTION

This invention relates to novel crystalline forms of mono-HCl salts and a mono-HCl salt hydrate of JNJ-26481585, an inhibitor of histone deacetylases. The invention also relates to processes for production of these forms, to intermediates used in these processes, to pharmaceutical compositions comprising these forms, and to the use of these forms in medical treatment for instance as a medicine to inhibit proliferative conditions, such as cancer and leukemia.

BACKGROUND ART

Many pharmaceutical solids can exist in different physical forms, e.g. in an amorphous form, in one or several crystal form(s) (e.g. anhydrous or solvated forms), in the form of mixture of different crystal forms, or as a mixture of an amorphous form and crystal form(s).

An amorphous form is a form in which a three-dimensional long-range order does not exist. In the amorphous form the position of the molecules relative to one another are essentially random, i.e. without regular arrangement of the molecules on a lattice structure. Amorphous and disordered materials often have improved properties, but generating and stabilising this state can be a big challenge.

A crystal or crystalline form is the form in which the position of the molecules relative to one another is organised according to a three-dimensional lattice structure. Crystalline forms typically include polymorphs and pseudopolymorphs. Polymorphs are different crystalline forms of the same compound resulting from different arrangement of the molecules in the solid state. Different polymorphs have different crystal structures due to a different packing of the molecules in the lattice. This results in a different crystal symmetry and/or unit cell parameters. Polymorphs differ from each other in their physicochemical parameters but not in their chemical composition. Polymorphism is usually difficult to control and poses challenges to the galenists. Pseudopolymorphs, also referred to as solvates, are a particular case of solid state crystalline forms in which either stoichiometric or non-stoichiometric amounts of solvent molecules are present or incorporated into the lattice structure of the compound. A water solvate is also referred to as a hydrate.

Solid state chemistry is of interest to the pharmaceutical industry and especially to those involved in the development of suitable dosage forms. For example, solid state transformations may seriously impact the stability of pharmaceutical drugs (shelf-life). A metastable pharmaceutical solid form can change into a crystalline structure (e.g. from amorphous to crystalline) or solvate/desolvate in response to changes in environmental conditions, processing, or over time.

Different crystal forms or amorphous form of the same drug may have substantial differences in such pharmaceutically important properties as dissolution rates, thermodynamic solubility and bioavailability. The rate of dissolution of an active ingredient in a patient's stomach fluid may have therapeutic consequences since it imposes an upper limit on the rate at which an orally-administered active ingredient may reach the patient's bloodstream. The rate of dissolution is thus a consideration in formulating solid dosage forms and liquid medicaments such as syrups and elixirs.

Likewise, different crystals or amorphous form may have different processing properties, such as hygroscopicity, flowability, compactation, and the like, which could affect their suitability as active pharmaceuticals for commercial production.

During the clinical development of pharmaceutical drugs, if the polymorphic form is not held constant, the exact dosage form used or studied may not be comparable from one lot to another. It is also desirable to have processes for producing a compound with the selected polymorphic form in high purity when the compound is used in clinical studies or commercial products since impurities present may produce undesired toxicological effects. Certain polymorphic forms may exhibit enhanced thermodynamic stability or may be more readily manufactured in high purity in large quantities, and thus are more suitable for inclusion in pharmaceutical formulations.

JNJ-26481585 has the following structure:

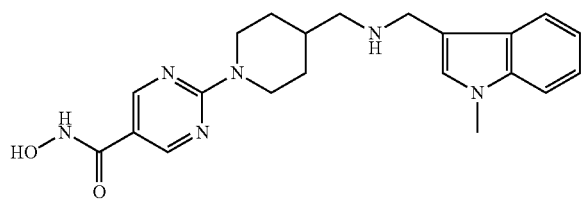 [SMILES: Cn1cc(CNCC2CCN(c3ncc(C(=O)NO)cn3)CC2)c2ccccc21]

The compound is an inhibitor of histone deacetylase (HDAC).

WO 2006/010750 published on 2 Feb. 2006 discloses an amorphous form of JNJ-26481585.$C_2HF_3O_2$ salt and a di-HCl salt and processes for obtaining them.

The synthesis of JNJ-26481585.$C_2HF_3O_2$ salt as originally described in WO 97/21701, is presented in scheme 1.

Therein, in step 1 intermediates of formula (III) were prepared by reacting an intermediate of formula (I) with the carboxaldehyde of formula (II), in the presence of sodium tetrahydroborate, in methanol.

In step 2 intermediates of formula (IV) were prepared by reacting an intermediate of formula (III) with sodium hydroxide in ethanol.

In step 3, intermediates of formula (V) were prepared by reacting an intermediate of formula (IV) with O-(tetrahydro-2H-pyran-2-yl)-hydroxylamine, in the presence of appropriate reagents such as N'-(ethylcarbonimidoyl)-N,N-dimethyl-1,3-propanediamine, monohydrochloride (EDC) and 1-hydroxy-1H-benzotriazole (HOBT). The reaction was performed in a mixture of dichloromethane and tetrahydrofuran.

In step 4, the hydroxamic acid $C_2HF_3O_2$ salt of formula (VI) was prepared by reacting the intermediate of formula (V), with trifluoro acetic acid. Said reaction was performed in methanol.

Scheme I
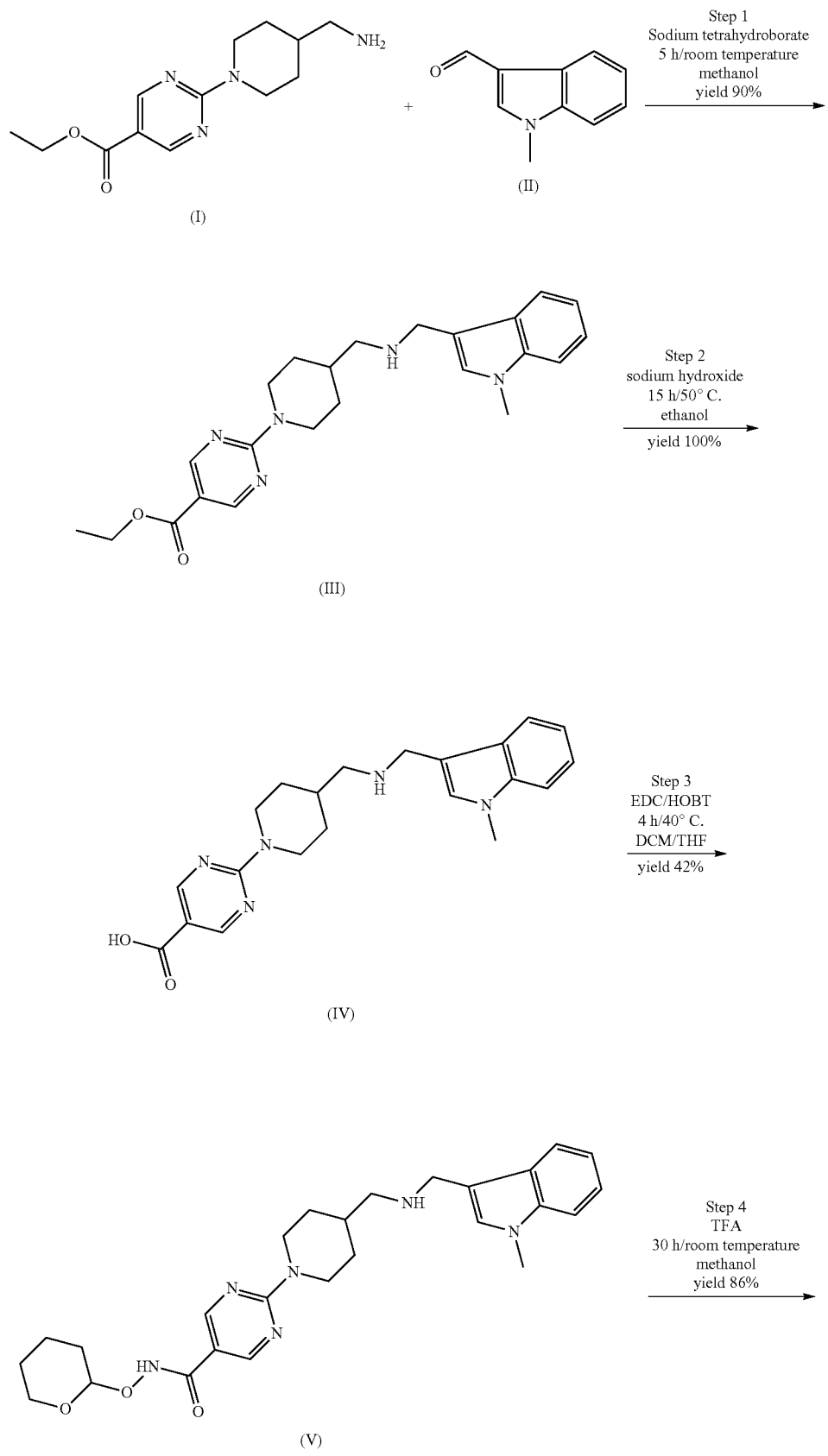

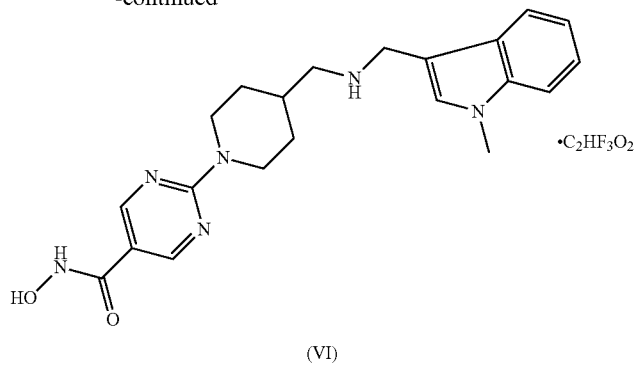

(VI)

Alternatively, the JNJ-26481585. 2HCl salt as originally described in WO 97/21701, was prepared by reacting the intermediate of formula (III), with hydroxylamine, in the presence of sodium hydroxide. Said reaction is performed in methanol, further conversion to the di-HCl salt was prepared in ethanol.

The process disclosed in WO 2006/010750 is unsuitable for large scale production as the consequence of low yields and high amount of impurities in the different process steps, which consequently requires several chromatographic steps. The purification of compounds using chromatography is expensive and environmentally unfriendly due to solvent consumption and the specialised equipment required to perform a large scale chromatography.

The problem solved by the present invention is the provision of novel crystalline forms of mono-HCl salts and a mono-HCl salt hydrate of JNJ-26481585. Another aspect of the present invention is a process wherein the novel crystalline HCl salt and HCl salt hydrate form are obtained in high yield and high purity. The advantageous properties of the present HCl forms are superior physicochemical properties including its non-hygroscopic nature and chemical stability enabling drugability of this compound.

DESCRIPTION OF THE FIGURES

FIG. 16 is an XPRD pattern overlay slurry conversion studies of the hydrate in ethanol at different temperatures

DESCRIPTION OF THE INVENTION

Preparation of the Intermediates

Figure 1:
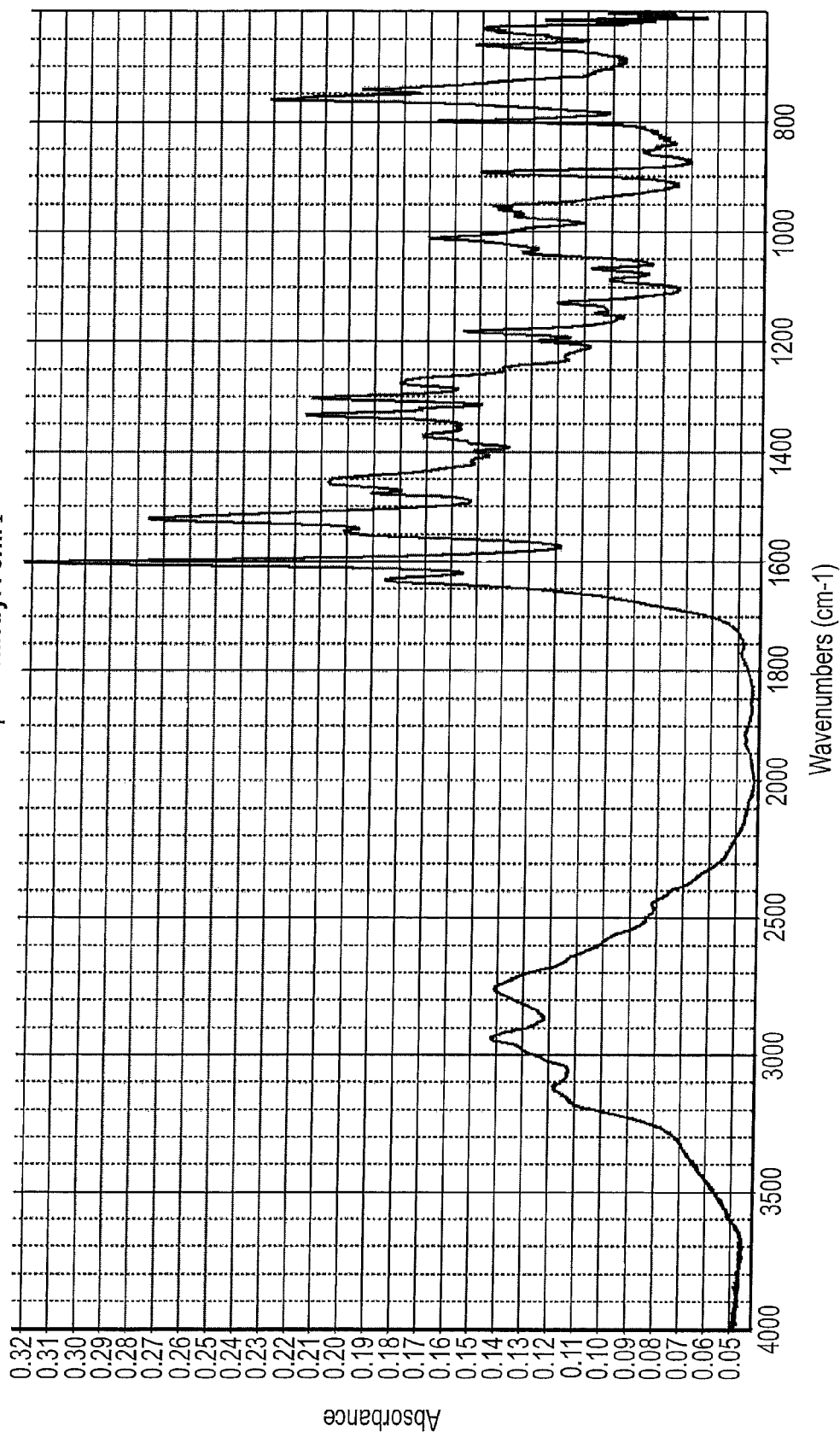
FIG. 1 is an Infrared (IR) spectrum representation of Form I

A. Preparation of the Intermediate of Formula (I)

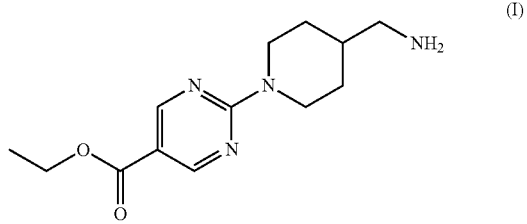 [SMILES: CCOC(=O)c1cnc(N2CCC(CN)CC2)nc1]

(I)

a) The intermediate of formula (XI) can be prepared by reacting an intermediate of formula (IX) with an intermediate of formula (X) in the presence of a suitable solvent such as a polar or apolar non-protic hydrocarbon solvent e.g. toluene, methylene chloride, isopropyl acetate, ethyl acetate, tetrahydrofuran and the like. Other aromatic or aliphatic aldehydes can be used in the process. This reaction can also be performed in protic solvents e.g. methanol, ethanol, isopropanol and the like. The reaction can be performed at a temperature between 25° C. and 60° C., preferably at a temperature of 45° C. Higher temperatures are not recommended due to potential instability of the intermediate of formula (X).

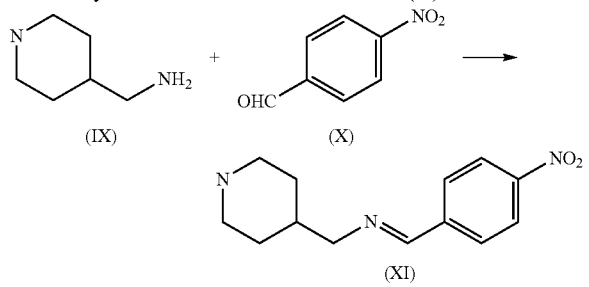

b) The intermediate of formula (VIII) can be prepared by converting the intermediate of formula (VII) in the presence of a suitable oxidant such as meta-chloroperoxy benzoic acid (MCPBA), in a suitable solvent such as a polar or apolar non-protic hydrocarbon solvent e.g. toluene, methylene chloride, isopropyl acetate, ethyl acetate, tetrahydrofuran and the like. The reaction can be performed at a temperature between −20° C. and 40° C., preferably at a temperature between 0° C. and 5° C. more preferably at 0° C. At higher temperatures meta-chloroperoxy benzoic acid is unstable and the intermediates of formula (VIII) may decompose. Complete conversion of intermediate (VII) into intermediate (VIII) can be obtained by addition of the appropriate amount of MCPBA. Thus the amount of MCPBA is preferably >1 equivalent.

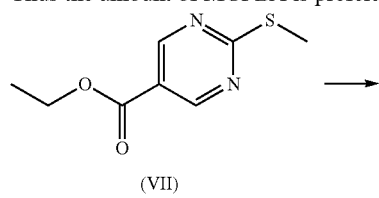

(VII)

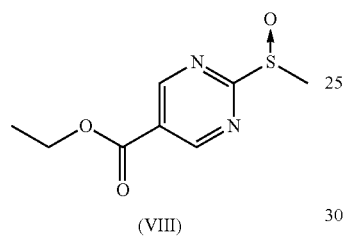

(VIII)

c) The intermediate of formula (I) can be prepared by reacting the intermediate of formula (VIII) with the intermediate of formula (XI) in the presence of a suitable solvent such as a polar or apolar non-protic hydrocarbon solvent or mixture thereof e.g. toluene, methylene chloride, isopropyl acetate, tetrahydrofuran, a mixture of diisopropylethylamine or other tertiary amine bases and ethylacetate and the like. The reaction can be performed at a temperature between −20° C. and 40° C., preferably at a temperature between 0° C. and 5° C. more preferably at 0° C. with warming up to 25° C.

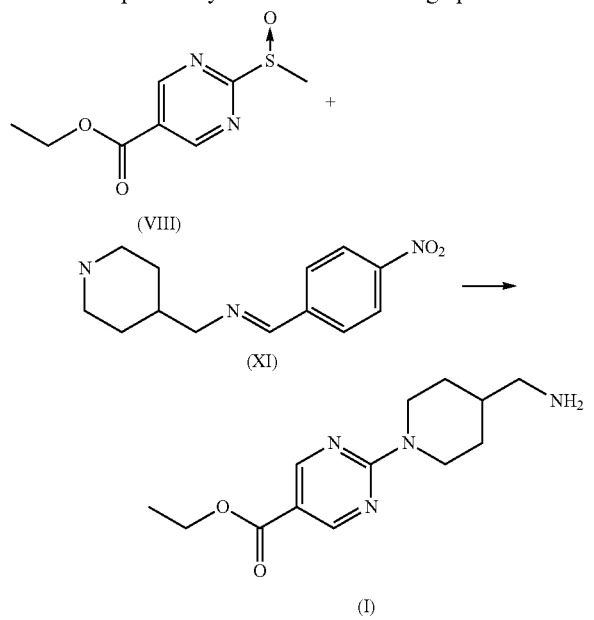

This synthesis with the temporary protection of the aminopiperidine of formula (IX) with the p-nitrobenzaldehyde of formula (X) with the formation of the intermediate of formula (XI), allows for the preferential reaction of the more substituted ring nitrogen. If this protection is not performed, large amounts of dimer (A) and isomer (B) are formed as both nitrogens of the intermediate of formula (IX) will react with the intermediate of formula (VIII). Warming up the reaction mixture overnight ensures complete reaction of the intermediate of formula (XI) to the intermediate of formula (I) and complete conversion of any remaining intermediate of formula (IX) to the dimer (A) which, together with remaining MCPBA, can be easily removed in the subsequent acidic workup.

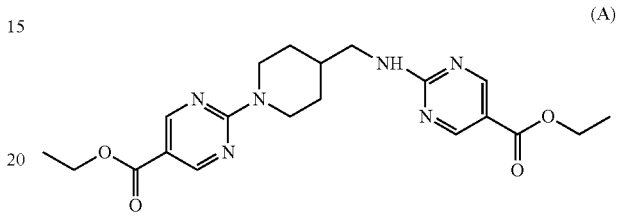

(A)

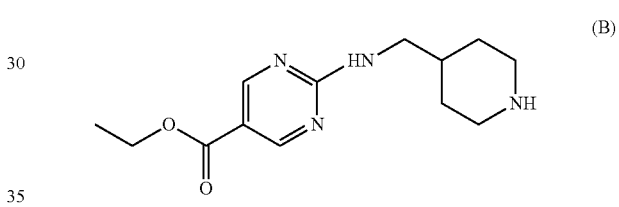

(B)

An embodiment of the present invention comprises the intermediate of formula (XI).

B. Preparation of the Intermediate of Formula (XIII)

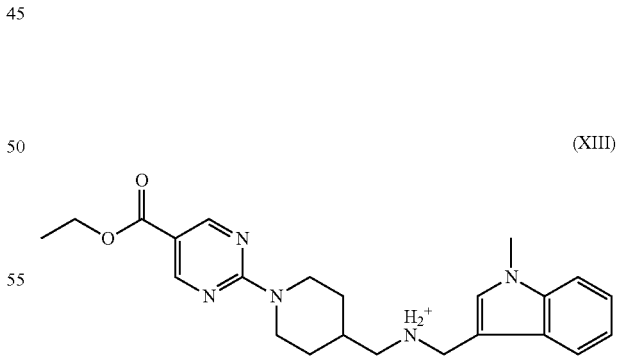

(XIII)

a) The intermediate of formula (XII) can be prepared by reacting the intermediate of formula (I) with the intermediate of formula (II) in a suitable solvent. The reaction can be performed at a temperature between 50° C. and 150° C., preferably at a temperature of 110° C. (reflux temperature of toluene). Azeotropic removal of water is required for this reaction to proceed. As solvent a polar or apolar non-protic hydrocarbon solvent can be used, such as toluene, isopropyl acetate and the like. These solvents azeotrope water well.

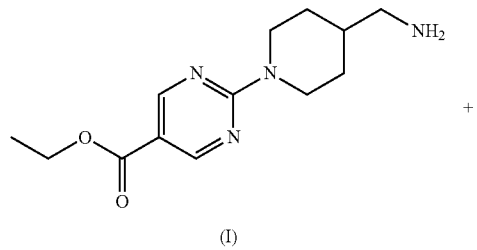

b) the intermediate of formula (XII) is treated with sodium tetrahydroborate in a suitable solvent such as polar or apolar non-protic and protic hydrocarbon solvents and mixtures thereof e.g. toluene, isopropyl acetate, ethanol, methanol, isopropanol and the like. The reduction with sodium tetrahydroborate can occur between 0° C. and 50° C., preferably at 10° C. Low temperature during reduction is preferred to avoid formation of over-reduced impurities c) Subsequently, salt formation is performed with fumaric acid in a mixture of acetone/ethanol with 5% v/v water, with the formation of the intermediate of formula (XIII).

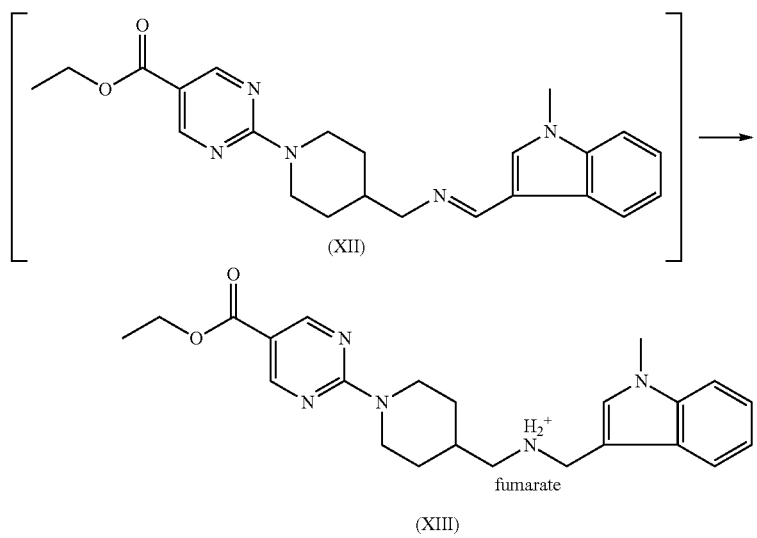

-continued

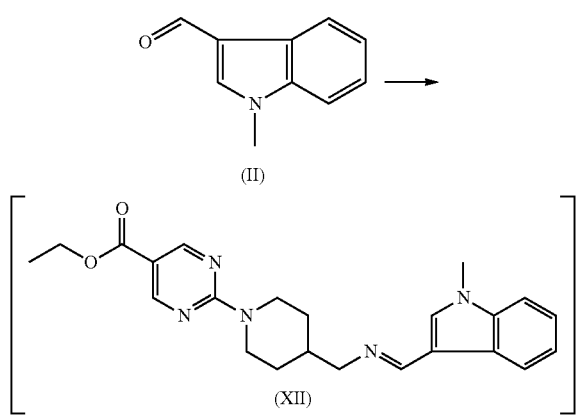

An embodiment of the present invention comprises the fumarate salt of formula (XIII).

C. Preparation of Intermediate of Formula (XVIII)

In a first attempt to find a better synthesis method for the production of JNJ-26481585, the intermediate of formula (III) was reacted with O-(tetrahydro-2H-pyran-2-yl)-hydroxylamine, in the presence of a base and a solvent but without coupling reagent. This attempt was not successful.

In a second attempt it was tried to protect the amino and hydroxamic acid moieties with acid labile protecting groups in order to effect simultaneous deprotection-salt formation.

Therefore the intermediate of formula (XIII) was converted to the free base, giving the intermediate of formula (III) and further converted to the intermediate of formula (XIV), wherein R is tertiair butyl, benzyl or fulveneyl followed by hydrolysis with NaOH in ethanol and isolation of the intermediate of formula (XV) by acidification and crystallization directly from the reaction mixture.

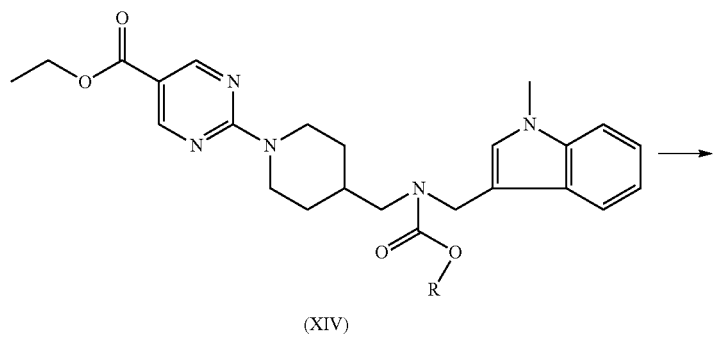

(XIV)

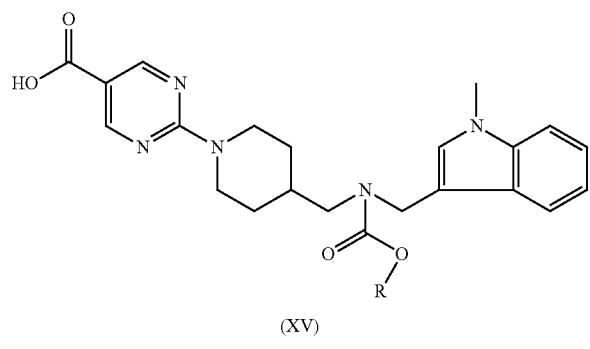

(XV)

Coupling of the intermediate of formula (XV) with O-(tetrahydro-2H-pyran-2-yl)-hydroxylamine under standard aminoacid coupling conditions (EDC, HOBT, triethylamine, tetrahydrofuran) afforded the intermediate of formula (XVI) in excellent yield. The coupling reaction for intermediates of formula (XV) wherein R is fulvenyl caused some cleavage of the fulvenyl-group due to the triethylamine needed for optimal coupling.

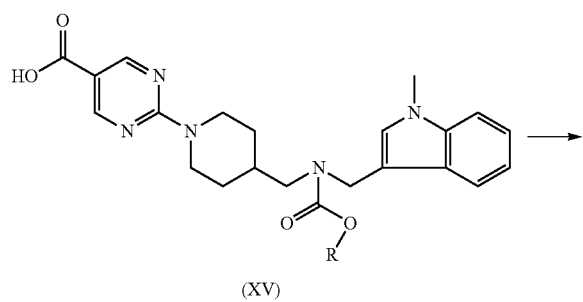

(XV)

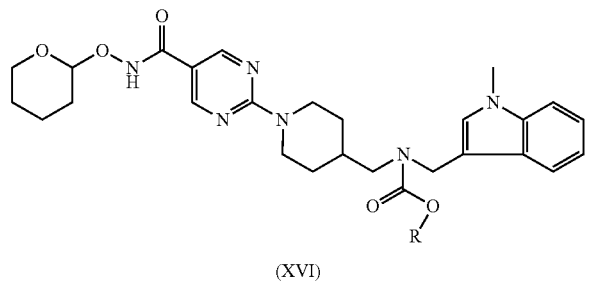

(XVI)

Attempts to deprotect the intermediate of formula (XVI), wherein R is tertiary butyl, were then undertaken under a variety of conditions (solvents: ethanol, ethylacetate, toluene, acetone, methyl isobutyl ketone, dimethylformamide; Acids: ethane sulfonic acid, methane sulfonic acid, hydrochloric acid, trifluoroacetic acid). Unfortunately either at ambient temperature (2-3 hours) or at 50° C. (10 min) the only products observed were products from cleavage of the indole moiety.

The hydrogenolysis of intermediates of formula (XVI), wherein R is benzyl, was attempted under hydrogen atmosphere and in the presence of an appropriate catalyst such as, for example, palladium-on-charcoal and was judged unsuccessful due to competing cleavage (up to 20%) of the N—O bond on the hydroxamic acid product. On the other hand, cleavage of the fulvenyl group of the intermediate of formula (XVI), wherein R is fulvenyl, herein referred to as the intermediate of formula (XVI-a) under mild conditions and trapping the fulvene by-product by using thiol silica gel was successful. The corresponding free amine of formula (V) can give the compound of formula (XIX) under similar conditions (1.05 equivalents of hydrochloric acid, ethanol, 70° C.) as described below.

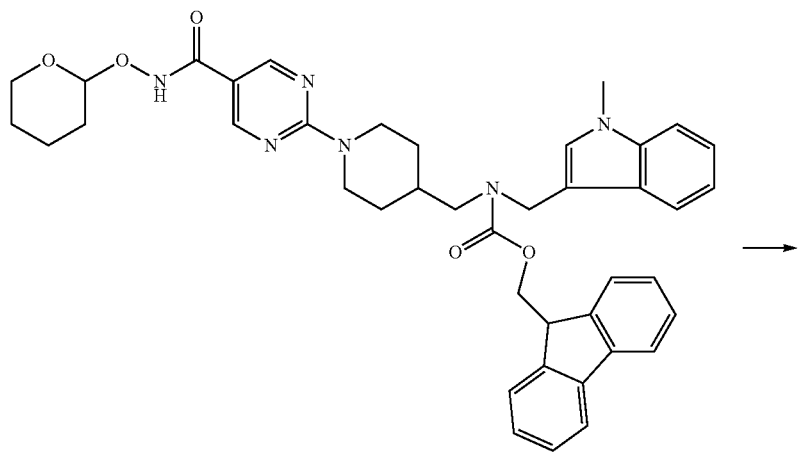

(XVI)

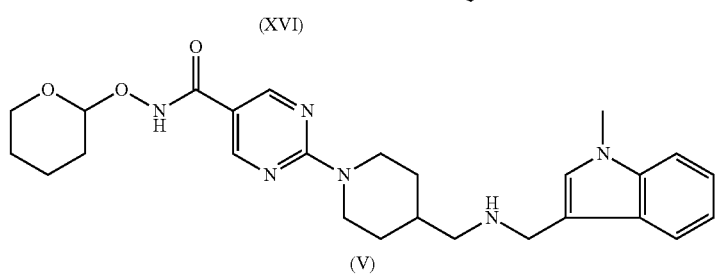

(V)

a) Finally, the free base of intermediate (XIII) can be obtained by an aqueous sodium hydroxide neutralization and extraction in methyltetrahydrofuran. The organic layer containing the free base is then submitted to a basic hydrolysis with 3 mole equivalents sodium hydroxides in water at reflux. The sodium salt in the water layer is then separated from the methyltetrahydrofuran layer and acidified with 5 mole equivalents HCl at 10° C.

The intermediate of formula (XVII) can have a variable water content. Immediately after drying the water content is 0.7%. When the sample was left 24 h at the atmosphere, the water content increased and stabilized at 8% water which represents 2 mole of water.

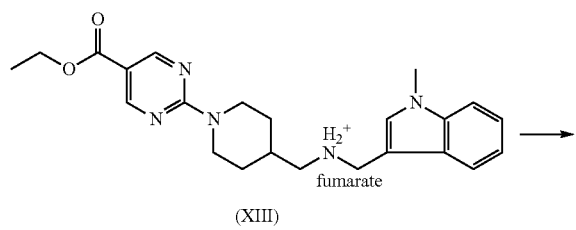

(XIII)

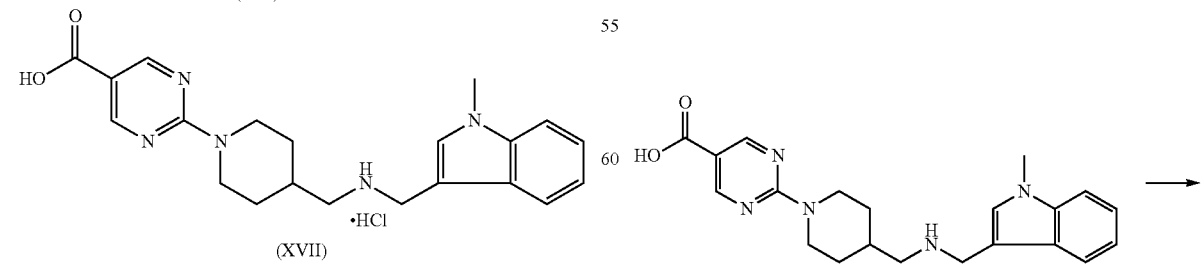

(XVII)　　　　　　　　　　　　　(XVII)

b) The effect of water in intermediate (XVII) is crucial, as the below coupling reaction requires a specific amount of water to be successful. The amount of water in intermediate (XVII) is preferably between 15 and 25 v/v %, most preferably ca 16 v/v %.

The intermediates of formula (XVIII) can be prepared by reacting the intermediate of formula (XVII) with O-(tetrahydro-2H-pyran-2-yl)-hydroxylamine, in the presence of appropriate reagents such as N'-(ethylcarbonimidoyl)-N,N-dimethyl-1,3-propanediamine, monohydrochloride (EDC) as coupling reagent. The reaction can be performed in polar or apolar non-protic and protic hydrocarbon solvents and mixtures thereof e.g. methyltetrahydrofuran, dimethylformamide (DMF), dichloromethane (DCM), toluene, isopropanol, ethanol, acetonitrile, ethyl acetate, isopropanol acetate, mixture thereof and mixture of one or more of the different solvents with water, preferably a mixture of ethylacetate and ethanol, more preferably a mixture of ethylacetate, ethanol and water. The temperature during the reaction can be between 10° C.-40° C., preferably at room temperature.

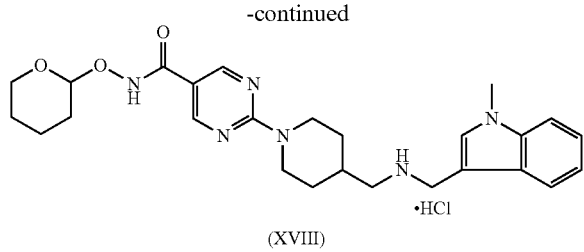

(XVIII)

The reaction is fast and complete when enough water is present. The reaction is slower under dry conditions, more impurities are present and the reaction rate towards product drops down.

c) The intermediate with formula (XVIII) can be dissolved in a solvent such as dimethylformamide or dimethylacetamide, preferably dimethylacetamide. Addition of a co-solvent allows the product to crystallize out. Co-solvents such as acetone, methyl isobutyl ketone or methyl ethyl ketone, preferably methyl isobutyl ketone, can be used. Purification can be performed at a temperature between 25° C.-90° C., preferably between 50° C. and 70° C. Crystallization time should not be longer than 5 h. At higher temperatures or longer crystallization periods the yield of the final product goes down. Recrystallization can be performed in a solvent such as ethanol in the presence of a co-solvent such as methyl ethyl ketone at a temperature between 50° C. and 70° C., preferably at 70° C.

An embodiment of the present invention comprises the hydrochloric salts of formula (XVII) and (XVIII)

Preparation of Crystalline Forms

The intermediate of formula (XVIII) can be converted into the HCl salt of formula (XIX) by adding hydrochloric acid in a suitable solvent such as ethanol or methanol while the reaction mixture is at the desired temperature.

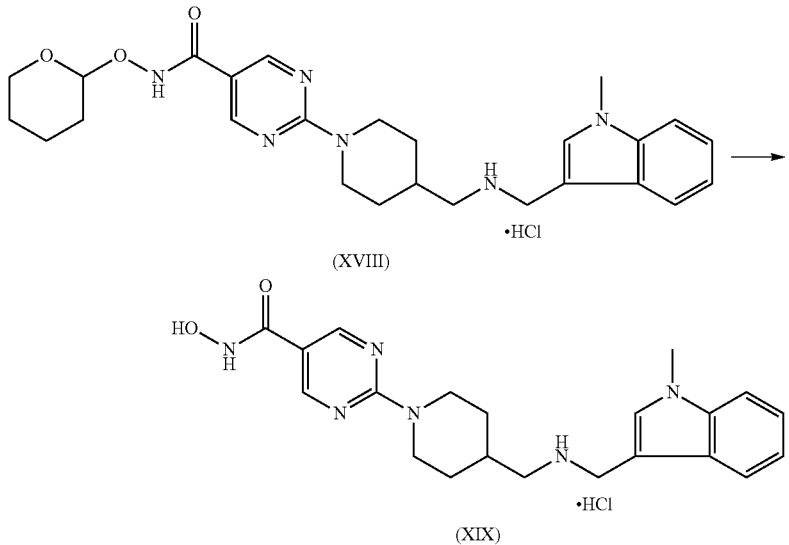

The present invention provides a process for preparing the crystalline mono-HCl salt Form I comprising:
a) dissolving compound of formula (XVIII) in an alcoholic solvent containing less than 0.1% w/w of water, while heating to between 50° C. and 70° C., preferably 50° C. and 60° C. of the solvent;
b) adding hydrochloric acid to the reaction mixture; and
c) stirring the reaction mixture while maintaining the temperature at between 50° C. and 70° C., preferably between 50° C. and 60° C. more preferably at 55° C.

In one embodiment, the process mentioned in the paragraph above for preparing Form I comprises adding ethanol or methanol in a concentration between 10.3 and 20.6 L/mol, preferably in a concentration of 10.3 L/mol.

In another embodiment, the processes mentioned above for preparing Form I comprises in step a) dissolving the compound in a time slot of 30 min to 3 h, preferable in a time slot of 30 min to 45 min.

In another embodiment, the processes mentioned above for preparing Form I comprises in step b) adding hydrochloric acid at a concentration of 0.05 to 0.4 equivalents of concentrated HCl preferably at a concentration between 0.05 to 1.1 equivalents, preferable at a concentration between 0.05 to 0.4 equivalents.

In another embodiment, the process mentioned in paragraph 1 to 3 above for preparing Form I comprises in step b) adding hydrochloric acid at a concentration of 0.03 to 0.07 equivalents of HCl (1 Molar) preferably at a concentration between 0.03 to 0.05 equivalents.

In another embodiment, the process mentioned in paragraph 1 to 3 above for preparing Form I comprises in step b) adding hydrochloric acid at a concentration of 0.03 to 0.05 equivalents of HCl in isopropanol.

In another embodiment, the processes mentioned above for preparing Form I comprises in step c) dissolving the compound in a time slot of 30 min to 3 h, preferable in a time slot of 30 min to 45 min.

In another embodiment, the processes mentioned above for preparing Form I comprises in step c) stirring the mixture between 30 min and 16 h, preferably for 16 h.

The present invention further provides a process for preparing the hydrate form comprising:
a) dissolving the compound of formula (XVIII), in an ethanol/water or methanol/water mixture comprising more than 5% of water, while heating to between 50° C. and 70° C., preferably 50° C. and 60° C. of the solvent;
b) adding hydrochloric acid to the reaction mixture; and c) stirring the reaction mixture while maintaining the temperature at between 50° C. and 70° C., preferably between 50° C. and 60° C. more preferably at 55° C.

In one embodiment, the process mentioned in the paragraph above for preparing the hydrate form comprises adding ethanol or methanol in a concentration between 10.3 and 20.6 L/mol, preferably in a concentration of 10.3 L/mol.

In another embodiment, the processes mentioned above for preparing the hydrate form comprises in step a) dissolving the compound in a time slot of 30 min to 3 h, preferable in a time slot of 30 min to 45 min.

In another embodiment, the processes mentioned above for preparing the hydrate form comprises in step b) adding hydrochloric acid at a concentration of 0.05 to 0.4 equivalents of concentrated HCl preferably at a concentration between 0.05 to 1.1 equivalents, preferable at a concentration between 0.05 to 0.4 equivalents.

In another embodiment, the process mentioned in paragraph 1 to 3 above for preparing the hydrate form comprises in step b) adding hydrochloric acid at a concentration of 0.03 to 0.0.07 equivalents of HCl (1 Molar) preferably at a concentration between 0.03 to 0.05 equivalents.

In another embodiment, the process mentioned in paragraph 1 to 3 above for preparing the hydrate form comprises in step b) adding hydrochloric acid at a concentration of 0.03 to 0.05 equivalents of HCl in isopropanol.

In another embodiment, the processes mentioned above for preparing the hydrate form comprises in step c) dissolving the compound in a time slot of 30 min to 3 h, preferable in a time slot of 30 min to 45 min.

In another embodiment, the processes mentioned above for preparing the hydrate form comprises in step c) stirring the mixture between 30 min and 16 h, preferably for 16 h.

The present invention further provides slurrying processes for preparing Form I comprising:

slurrying Form II in a solvent selected from ethanol or methanol at a temperature of at least 50° C., preferably at 70° C. or higher; or slurrying a mixture of Form I and Form II in a solvent selected from ethanol or methanol at a temperature of at least 50° C., preferably at 70° C. or higher.

In another embodiment, the slurrying processes mentioned above for preparing Form I may comprise 10% of water, preferably <2% of water most preferably <0.07% of water.

In another embodiment, the slurrying processes for preparing Form I further comprise stirring during at least 4 to 7 days.

The present invention further provides slurrying processes for preparing the hydrate form comprising:

slurrying Form II in an ethanol/water or methanol/water mixture comprising at least 10% of water;

slurrying a mixture of Form I and Form II in an ethanol/water or methanol/water mixture comprising at least 10% of water;

slurrying a mixture of Form I and Form II in an aqueous medium comprising at least 90% of water.

In another embodiment, the slurrying processes for preparing the hydrate form further comprise stirring during 4 to 7 days.

In another embodiment, the processes for preparing Form I further comprise filtering the precipitates obtained after slurrying Form II in an alcoholic solvent, or after slurrying a mixture of Form I and Form II in a solvent as indicated above.

In another embodiment, the slurrying processes for preparing Form I further comprise, after the filtering step of the paragraph above, washing the filtered precipitates obtained after slurrying Form II in an alcoholic solvent, or after slurrying a mixture of Form I and Form II in a solvent as indicated above, wherein the washing step is performed with the same solvent employed during the slurrying step.

For the preparation of any of the Forms of the present invention, which proceeds from a solution of the compound of formula (XVIII), it should be recognized by those skilled in the art that the solid form of the starting material has no influence on the solid form of the end product and control of the resulting solid Form is performed via the control of the process parameters.

The invention provides as well the above processes for preparing Form I comprising between step a) and b) seeding the mixture with Form I.

The invention provides as well the above processes for preparing the hydrate form comprising between step a) and b) seeding the mixture with Form I.

The invention provides as well a process wherein the obtained crystalline form is isolated by filtration or centrifugation, optionally combined with washing and drying.

The starting material used for the processes of the present invention may be any crystalline form of the compound of formula (XVIII).

With the term "compounds of the present invention" is meant a compound of formula (XI), (XIII), (XVII), (XVIII) or (XIX).

In one embodiment, the solvents employed in the preparation of the crystalline forms of the present invention are pharmaceutically acceptable solvents. In another embodiment, the solvents employed in the preparation of the crystalline forms of the present invention are pharmaceutically non-acceptable solvents since they may also find their use in the preparation of pharmaceutically acceptable polymorphs.

The processes for the production of the crystal forms of the present invention typically include obtaining a crystalline solid material from a solution or dispersion of the compound of formula (XIX) in a solvent medium, or from slurrying the compound of formula (XIX).

One skilled in the art would appreciate that the conditions concerning crystallization may be modified in order to improve the crystallization process or to induce precipitation, and without affecting the form of the polymorph obtained. These conditions may include bringing the solution, dispersion, or slurry of compound of formula (XVIII) or (XIX) and the solvent(s) to a desired concentration, bringing the said solution, dispersion, or slurry to a desired temperature, adding the desired concentration of hydrochloric acid, adding crystal seeds, effecting any suitable pressure, removing and/or separating any undesired material or impurities, drying the formed crystals to obtain the polymorphs in a solid state, if such state is desired.

A preferred way of inducing precipitation is to reduce the solubility of the compounds of the invention. The solubility of the compound may be reduced, for example, by adding an anti-solvent.

Bringing the solution, dispersion, or slurry of the compounds of the invention and solvents to a desired concentration does not necessarily imply an increase in the concentration of the compounds of the invention. In certain cases, a decrease or no change in concentration of the compound of the invention could be preferable. The techniques used for obtaining a desired concentration are those common in the art, for instance, evaporation by atmospheric distillation, vacuum distillation, fractioned distillation, azeotropic distillation, film evaporation, heating, cooling, other techniques well known in the art and combinations thereof. An optional process for obtaining a desired concentration could as well involve the saturation of the solution of the compounds of the invention and solvents, for example, by adding a sufficient volume of a non-solvent to the solution to reach the saturation point. Other suitable techniques for saturating the solution include, by way of example, the introduction of additional compound of the invention to the solution and/or evaporation of a portion of the solvent from the solution. As referred to herein, a saturated solution encompasses solutions at their saturation points or exceeding their saturation points, i.e. supersaturated. A nearly saturated solution refers to solutions that are near saturation but have not reached their saturation points.

A way to improve the crystallization process of the present invention, in particular of accelerating crystallization, is by seeding with a crystal of the product or scratching the inner surface of the crystallization vessel with a glass rod. Other times, crystallization may occur spontaneously without any inducement. The present invention encompasses both embodiments where crystallization of a particular form of compound of formula (XIX) occurs spontaneously, or is induced or accelerated, unless if such inducement or acceleration is critical for obtaining a particular form.

The term "seeding" refers to the addition of a crystalline material to facilitate crystallization. The term "crystal seeds" means powder of a previously obtained crystalline form of the compound of formula (XIX). Particular crystal seeds or seeding material of the present invention, which can be useful for preparing Form I, are the following:

crystal seeds of a mixture of Form I of compound (XIX) and the compound of formula (XVIII);

crystal seeds of Form I; or crystal seeds of Form II.

By bringing the said solution, dispersion, or slurry to a desired temperature, one will understand the acts of heating, cooling or leaving at ambient temperature. Warming of the solution, dispersion, or slurry may be necessary to completely dissolve the compounds of the invention.

Removing and/or separating any undesired material or impurities may be performed by purification, filtering, washing, precipitation or similar techniques. Separation, for example, can be conducted by known solid-liquid separation techniques. Filtering procedures known to those skilled in the art can as well be used in the present process. The filtrations can be performed, amongst other methods, by passing the solution, dispersion, or slurry through paper, sintered glass filter or other membrane material, by centrifugation, or using Buchner style filter, Rosenmund filter or plates, or frame press. Preferably, in-line filtration or safety filtration may be advantageously intercalated in the processes disclosed above, in order to increase the purity of the resulting polymorphic form. Additionally, filtering agents such as silica gel, Celite®, Arbocel®, dicalite diatomite, or the like, may also be employed to separate impurities from the crystals of interest.

Crystals obtained may be also dried, and such drying process may optionally be used in the different crystallization passages, if more than one crystallization passage is applied. Drying procedures include all techniques known to those skilled in the art, such as heating, applying vacuum, circulating air or gas, adding a desiccant, freeze-drying, spray-drying, evaporating, or the like, or any combination thereof.

Processes for crystallization of polymorphs of the compound of formula (XIX) may embrace multiple combinations of techniques and variations thereof. As such, and by way of example, crystallization of polymorphs of compound of formula (XIX) may be executed by dissolving, dispersing, or slurrying compound of formula (XIX) at a suitable temperature in the solvent whereby portion of the said solvent evaporates increasing the concentration of the compound of formula (XIX) in the said solution, dispersion, or slurry, cooling the said mixture, and optionally washing and/or filtering and drying the resulting crystals of compound of formula (XIX). Optionally, polymorphs of compound of formula (XIX) may be prepared by dissolving, dispersing, or slurrying compound of formula (XIX) in a solvent medium, cooling said solution, dispersion, or slurry and subsequently filtering and drying the obtained polymorph. Another example of preparation of crystal forms of compound of formula (XIX) could be by saturating compound of formula (XIX) in the solvent medium, and optionally filtering, washing and drying obtained crystals.

Crystal formation may as well involve more than one crystallization process. In certain cases, one, two or more extra crystallization steps may be advantageously performed for different reasons, such as, to increase the quality of the resulting crystal form.

By dissolving, dispersing, or slurrying the compound of the invention in the solvent, one may obtain different degrees of dispersion, such as suspensions, slurries or mixtures; or preferably obtain homogeneous one-phase solutions. The term "suspension" refers to a two-phase system consisting of a finely divided solid, in amorphous, crystalline form, or mixtures thereof, dispersed (suspended) in a liquid or dispersing medium, usually the solvent. The term "slurry" refers to a suspension formed when a quantity of powder is mixed into a liquid in which the solid is only slightly soluble (or not soluble). "Slurrying" refers to the making of a slurry.

Optionally, the solvent medium may contain additives, for example one or more dispersing agents, surfactants or other additives, or mixtures thereof of the type normally used in the preparation of crystalline suspensions and which are well documented in the literature. The additives may be advantageously used in modifying the shape of crystal by increasing the leniency and decreasing the surface area.

The solvent medium containing the solid may optionally be stirred for a certain period of time, or vigorously agitated using, for example, a high shear mixer or homogeniser or a combination of these, to generate the desired particle size for the organic compound.

Control of precipitation temperature and seeding may be additionally used to improve the reproducibility of the crystallization process, the particle size distribution and form of the product. As such, the crystallization can be effected without seeding with crystals of the compound of the formula (XIX) or preferably in the presence of crystals of the compound of the formula (XIX), which are introduced into the solution by seeding. Seeding can also be effected several times at various temperatures. The amount of the seed material depends on the scale of the experiment and can readily be determined by a person skilled in the art. Typically, the amount of seeding material is about 0.1 to 1 weight % of the amount of crystalline material expected from the reaction.

The time for crystallization in each crystallization step will depend on the conditions applied, the techniques employed and/or solvents used.

Breaking up the large particles or aggregates of particles after crystal conversion may additionally be performed in order to obtain a desired and homogeneous particle size. Accordingly, the crystals, powder aggregates and coarse powder of the polymorphic forms of compound of formula (XIX) may be optionally milled and sorted by size after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, microcrystals.

A preferred apparatus for milling or grinding is a fluid energy mill, or micronizer, because of its ability to produce particles of small size in a narrow size distribution. Micronizers use the kinetic energy of collision between particles suspended in a rapidly moving fluid stream to cleave the particles. An air jet is a preferred fluid energy mill. The suspended particles are injected under pressure into a recirculating particle stream. Smaller particles are carried aloft inside the mill and swept into a vent connected to a particular size classifier such as a cyclone. One of skill in the art would appreciate that some crystalline forms may undergo a transition to another form during particle size reduction.

Characterization of the Crystalline Forms

The present invention provides mono-HCl salts of formula (XIX) in solid state further characterized in that it is in crystalline form. In one embodiment, the invention provides the crystalline forms of the compound of formula (XIX) selected from Form I, Form II and the hydrated form. These forms are substantially free from impurities. Suitably, these forms contain no more than 10% of impurities, more suitably they contain no more than 5% of impurities, even more suitably they contain no more than 1% of impurities. Polymorphic purity may be tested by XPRD, with the area under the peaks used to calculate polymorphic purity. These forms are essentially pure. With the term "essentially pure" is meant more than 90% pure, suitably more than 95% pure, more suitably more than 97% pure, most suitably more than 99% pure.

The present invention further provides a mixture of two or more crystalline forms of compound of formula (XIX), wherein the crystalline forms are selected from Form I, Form II and the hydrated form.

In one embodiment, there is provided a mixture comprising Form I and Form II of compound of formula (XIX).

In another embodiment, there is provided a mixture comprising Form I and the hydrated form of the compound of formula (XIX).

In another embodiment, there is provided a mixture comprising the hydrated form and Form II of the compound of formula (XIX).

In another embodiment, there is provided a mixture comprising Form I, the hydrated form and form II of the compound of formula (XIX).

The present invention further provides a mixture of one or more crystalline forms of compound of formula (XIX) and an amorphous form of a non HCl salt of the compound of formula (XIX), wherein the crystalline forms are selected from Form I, Form II, and the hydrated form.

The characterising XPRD intensity peak positions of Form I, Form II and the hydrate form are given in degrees 2-theta.

Form I of compound (XIX) is characterized by typical diffraction peaks at two-theta positions 15.1°±0.2°, 17.2°±0.2°, 23.4°±0.2°, 24.4°±0.2° and 27.7°±0.2°. Form I is further characterized by X-ray powder diffraction peaks at two-theta positions 7.6°±0.2°, 12.0°±0.2° and 12.5°±0.2°.

Form II of compound (XIX) is characterized by typical diffraction peaks at two-theta positions 10.8°±0.2°, 13.7°±0.2°, 17.8°±0.2° and 26.7°±0.2. Form II is further characterized by X-ray powder diffraction peaks at two-theta positions 7.4°±0.2° and 22.9°±0.2°.

The hydrate form of compound (XIX) is characterized by typical diffraction peaks at two-theta positions 10.0°±0.2°, 13.4°±0.2° and 26.5°±0.2°. The Hydrate is further characterized by X-ray powder diffraction peaks at two-theta positions 21.6°±0.2° and 24.9°±0.2°.

Figure 2:
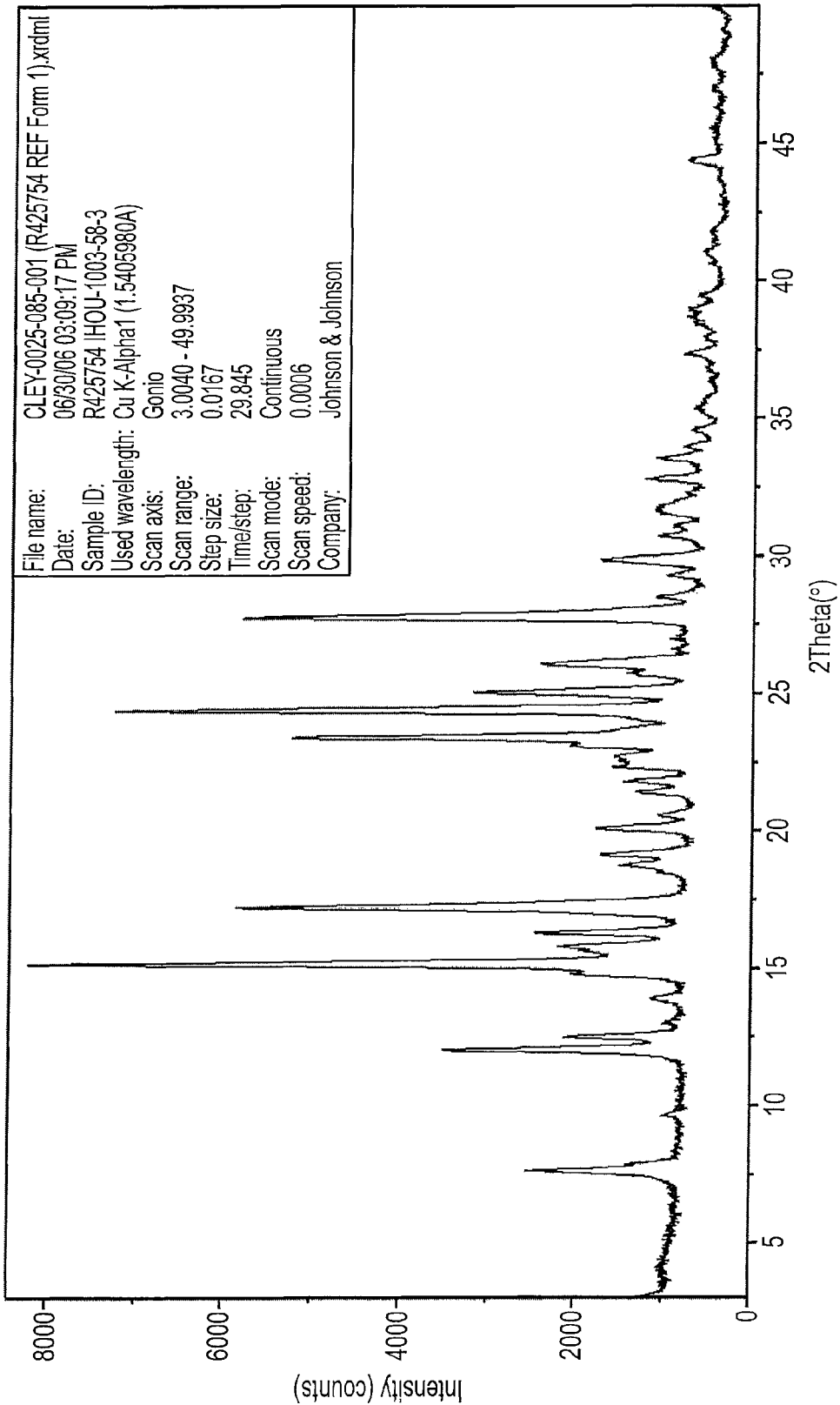
FIG. 2 is an X-ray powder Diffraction (XPRD) pattern representation of Form I
Figure 7:
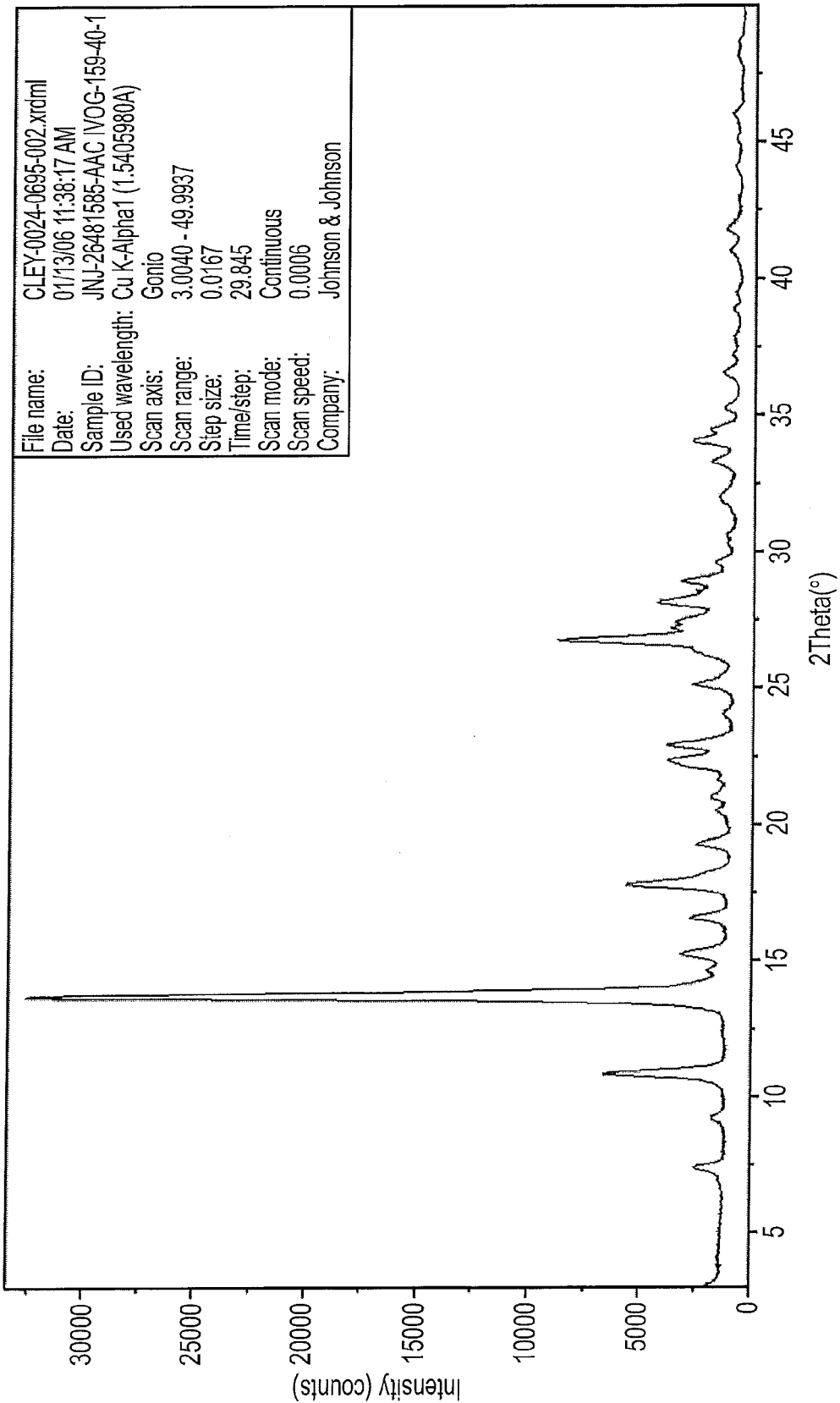
FIG. 7 is an XPRD pattern representation of Form II
Figure 12:
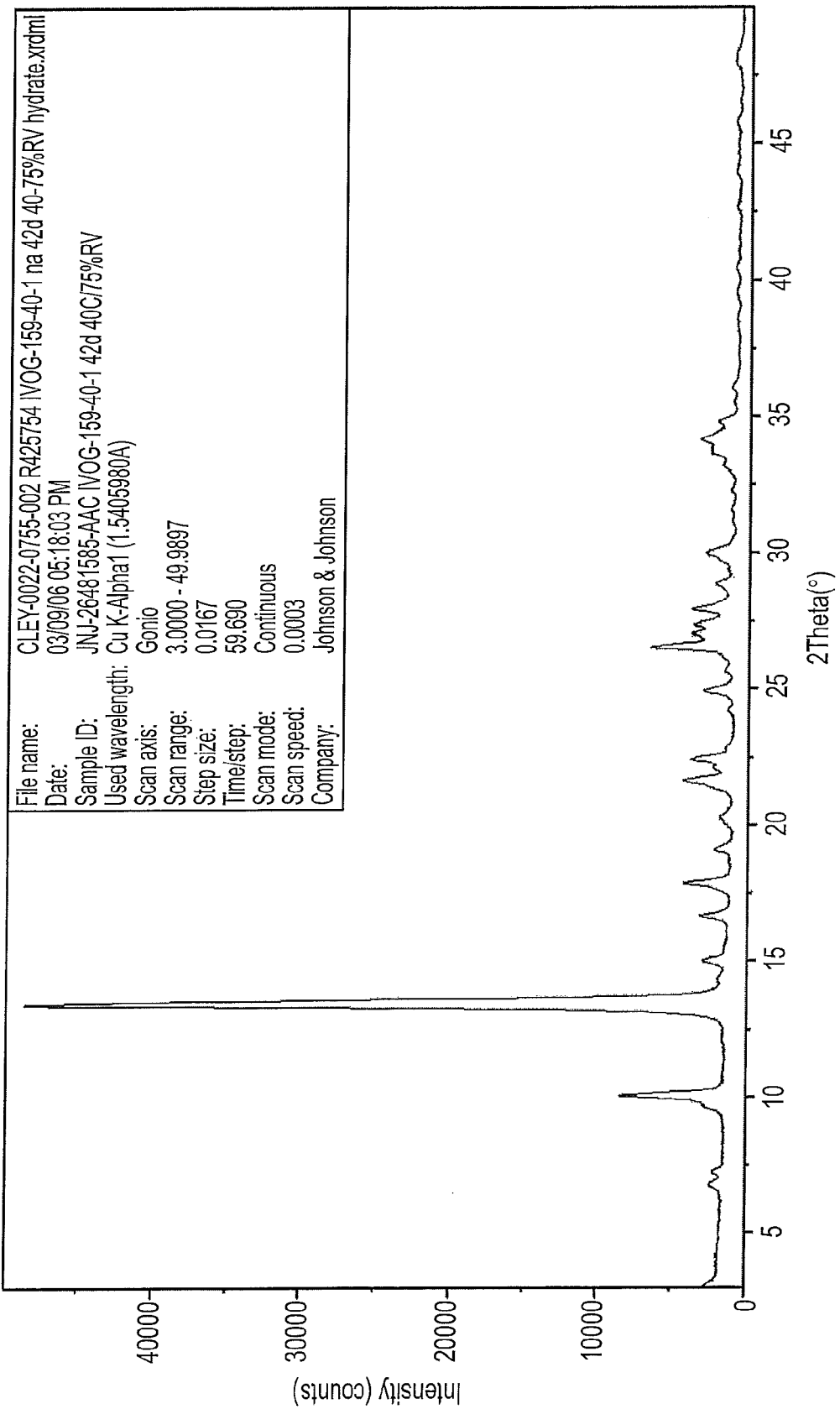
FIG. 12 is an XPRD pattern representation of the hydrate form
Figure 13:
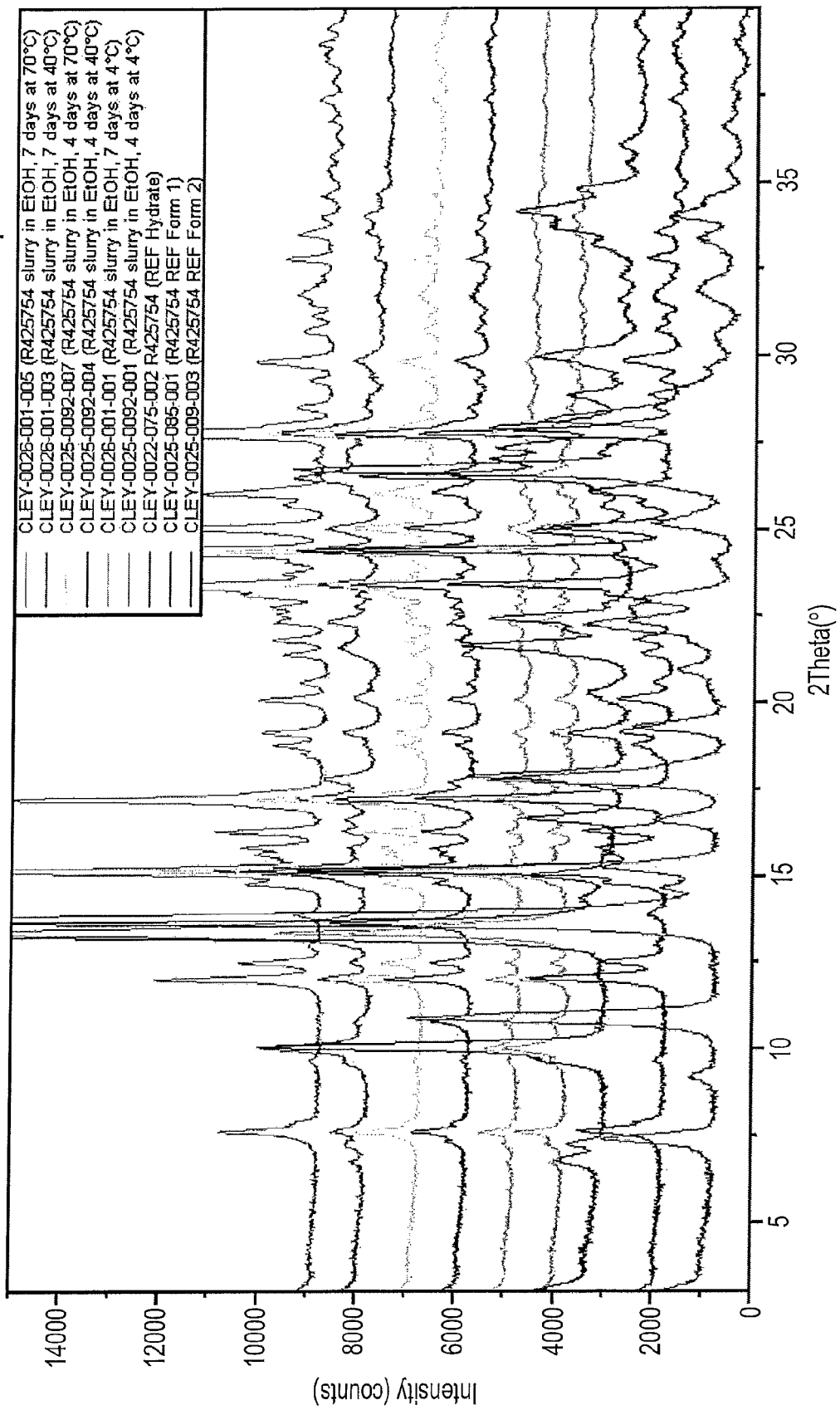
FIG. 13 is an XPRD pattern overlay slurry conversion studies of Form I and Form II in ethanol at different temperatures
Figure 14:
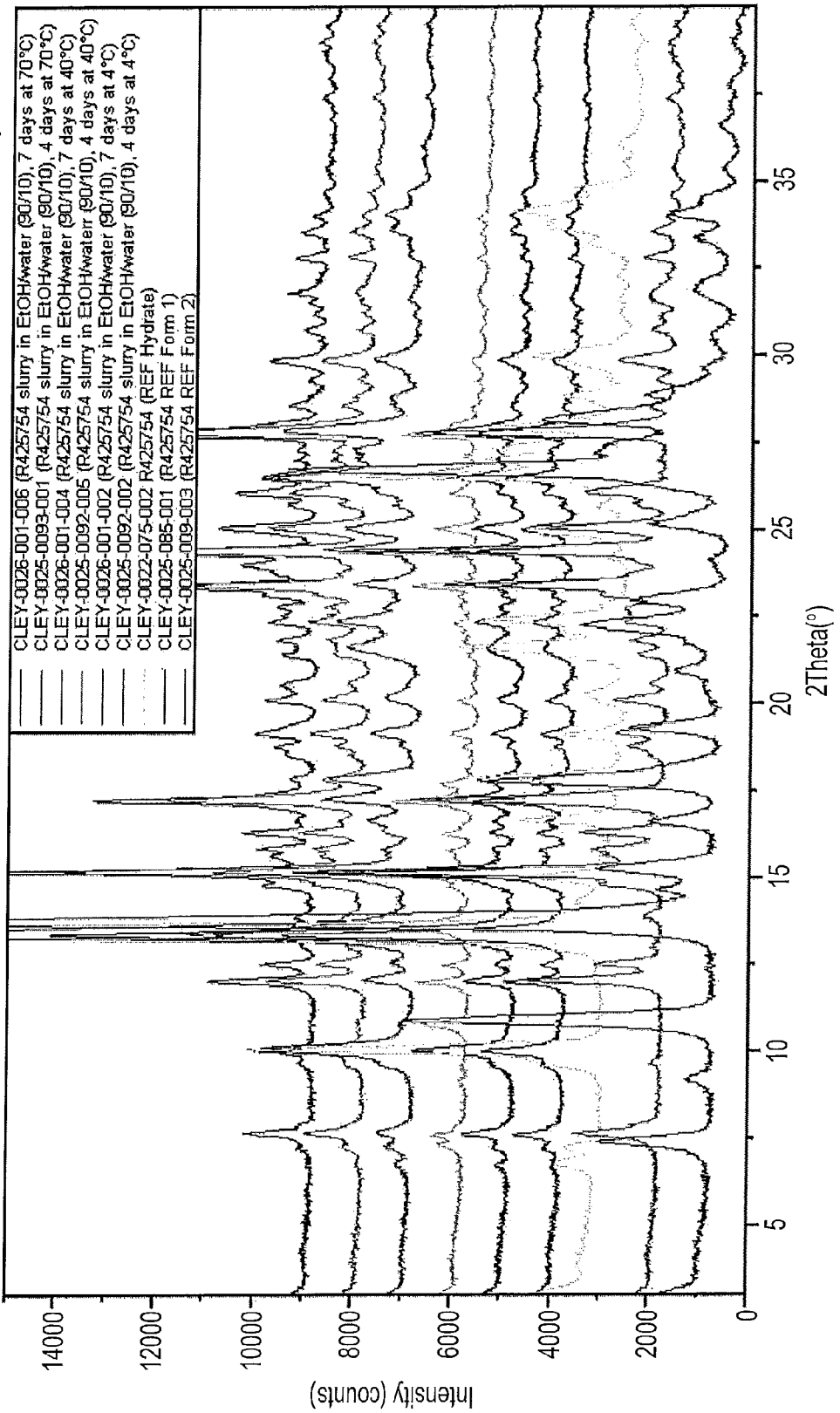
FIG. 14 is an XPRD pattern overlay slurry conversion studies of Form I and Form II in ethanol/water (90/10, v/v %) at different temperatures
Figure 15:
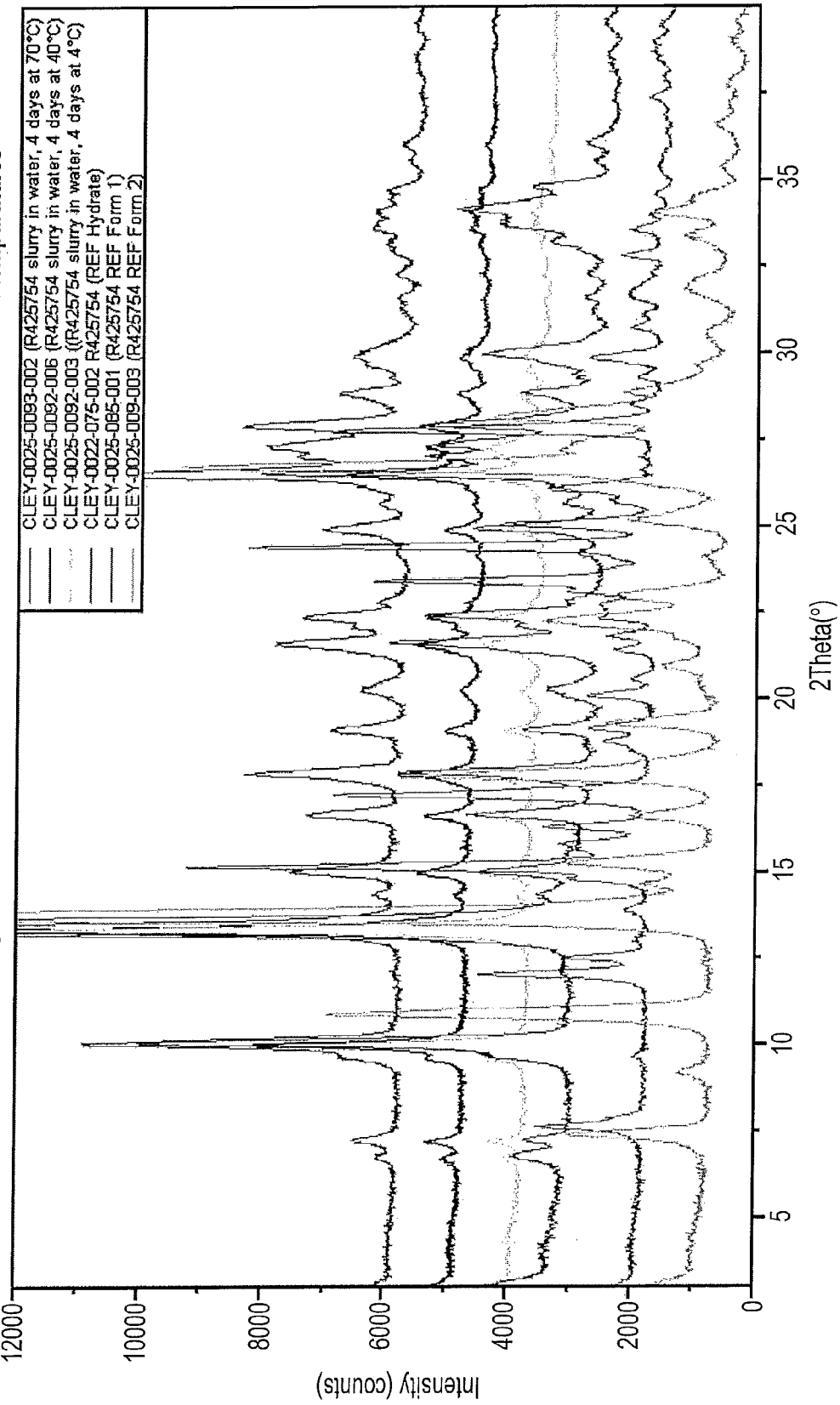
FIG. 15 is an XPRD pattern overlay slurry conversion studies of Form I and Form II in water at different temperatures

The X-ray powder diffraction pattern (XPRD) of Form I is as substantially depicted in FIG. 2. The X-ray powder diffraction pattern of Form II is as substantially depicted in FIG. 7. The X-ray powder diffraction pattern of the hydrated form is as substantially depicted in FIG. 12.

The XPRD data and pattern representations of all forms were obtained using a Philips X'PertPRO MPD diffractometer PW3050/60 with a generator PW3040. The instrument was equipped with a Cu LFF X-ray tube PW3373/00. The compound to be analysed was spread on a zero background sample holder. The instruments parameters were as follows:

generator voltage: 45 kV
generator amperage: 40 mA
geometry: Bragg-Brentano
stage: spinner stage.

The scanning parameters for Forms I, II and the hydrated form were as follows: the range was 3° to 50° 2-theta with a continuous scan at a rate of 0.01675°/step, at 29.845 sec/step. The spinner revolution time was 1 sec, the radiation type CuKα, and the radiation wavelength was 1.54056 Å.

The scanning parameters for Forms I and II were as follows: the range was 3° to 50° 2-theta with a continuous scan at a rate of 0.01675°/step, at 29.845 sec/step. The spinner revolution time was 1 sec, the radiation type CuKα, and the radiation wavelength was 1.54056 Å.

The scanning parameters for the hydrated form was as follows: the range was 3° to 50° 2-theta with a continuous scan at a rate of 0.01675°/step, at 59.690 sec/step. The spinner revolution time was 1 sec, the radiation type CuKα, and the radiation wavelength was 1.54056 Å.

The Incident beam path parameters for Forms I, II and the hydrated form were as follows:

program. divergence slit: 15 mm
Soller slit: 0.04 rad
beam mask: 15 mm
anti scatter slit: 1°
beam knife: +

The diffracted beam path parameters for Forms I, II and the hydrated form were as follows:

long anti scatter shield: +
Soller slit: 0.04 rad
Ni filter: +
detector: X'Celerator The accuracy of the XPRD peak positions provided for Forms I, II and the hydrated form is defined as 0.2° due to experimental differences, such as instrumentations, sample preparations, and the like.

The characterising IR absorbance peak positions of Forms I, II and the hydrated form are given in wavenumbers $cm^{-1}$.

Form I of compound (XIX) is characterized by an infrared spectrometry (IR) micro attenuated reflectance spectrum with typical absorption bands at 3119±2 $cm^{-1}$, 2756±2 $cm^{-1}$, 1634±2 $cm^{-1}$, 1475±2 $cm^{-1}$, 1371±2 $cm^{-1}$, 1333±2 $cm^{-1}$, 1275±2 $cm^{-1}$, 1226±2 $cm^{-1}$, 1128±2 $cm^{-1}$ and 1066 $cm^{-1}$±2 $cm^{-1}$.

Form II of compound (XIX) is characterized by an infrared spectrometry micro attenuated reflectance spectrum with typical absorption bands at about 3553±2 $cm^{-1}$, 3203±2 $cm^{-1}$, 3014±2 $cm^{-1}$ and 1541 $cm^{-1}$±2 $cm^{-1}$.

The hydrate form of compound (XIX), after 42 days storage at 40° C./75% relative humidity, is characterized by an infrared spectrometry micro attenuated reflectance spectrum with typical absorption bands at about 3558±2 $cm^{1}$, 3238±2 $cm^{-1}$, 1607±2 $cm^{-1}$ and 997 $cm^{-1}$±2 $cm^{-1}$.

Figure 6:
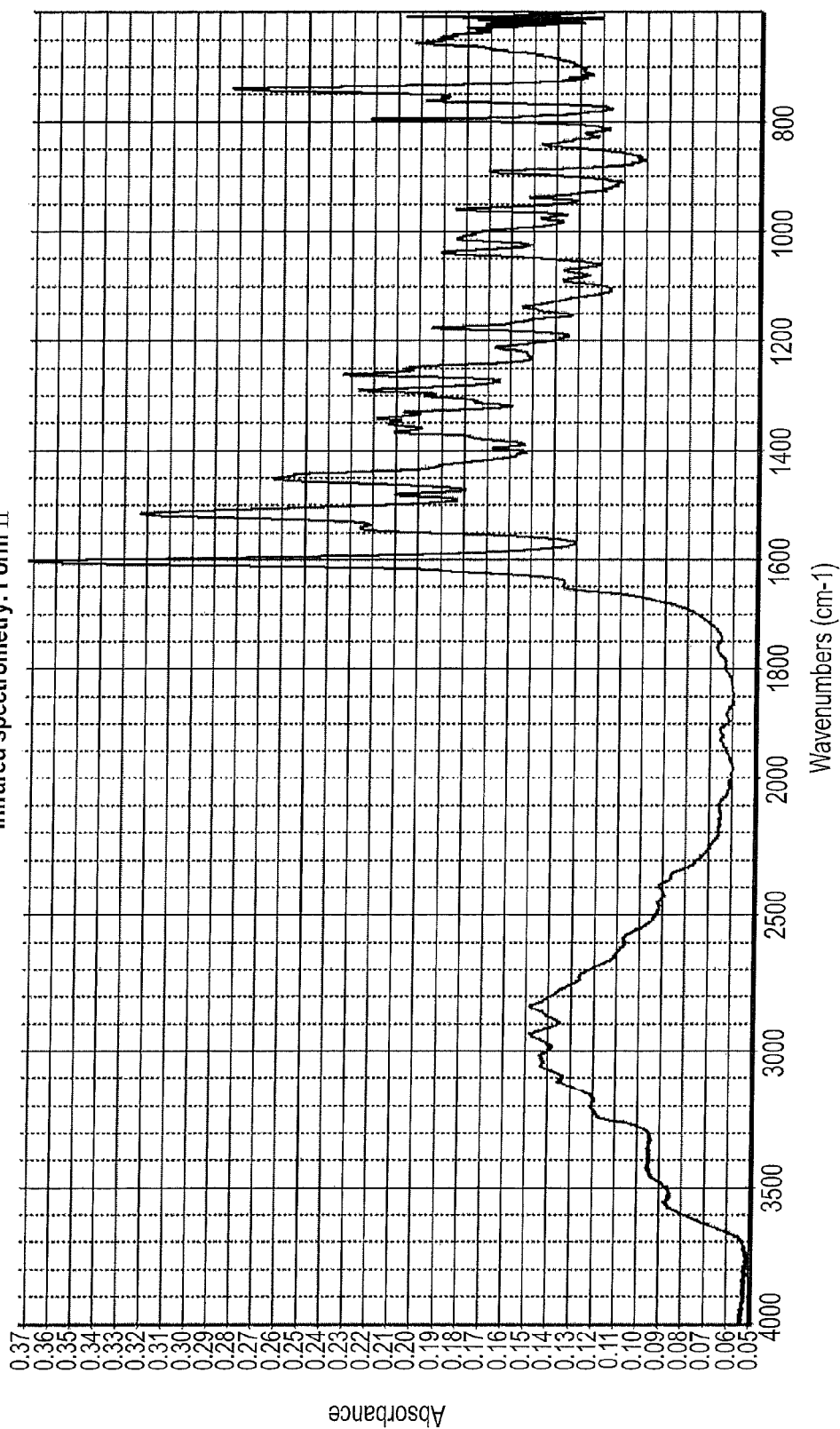
FIG. 6 is an IR spectrum representation of Form II
Figure 11:
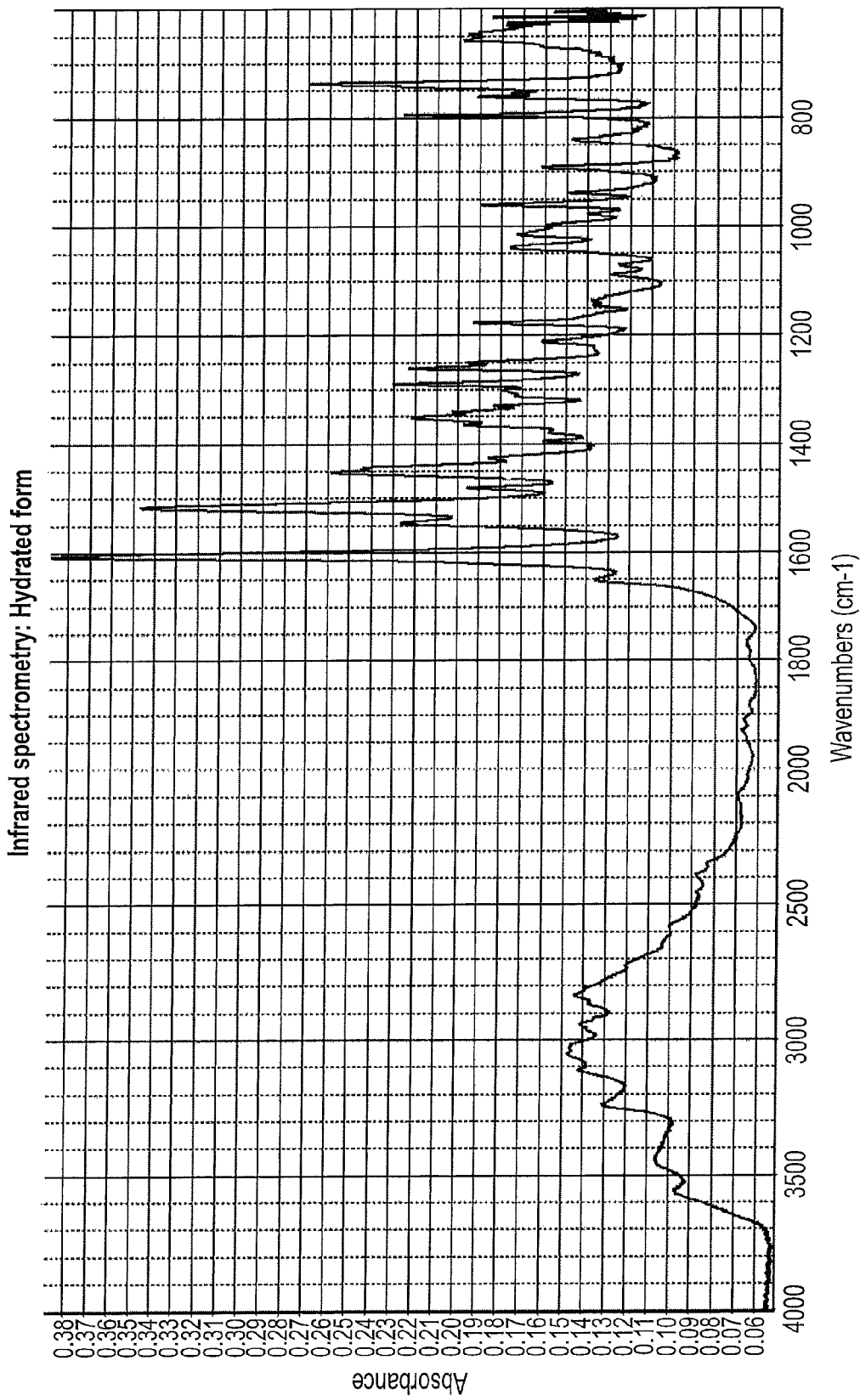
FIG. 11 is an IR spectrum representation of the hydrate form

The IR pattern of Form I is as substantially depicted in FIG. 1. The IR pattern of Form II is as substantially depicted in FIG. 6. The IR pattern of the hydrate form is as substantially depicted in FIG. 11.

The IR data and pattern representations were obtained using infrared spectrometry micro Attenuated Total Reflectance (microATR) with a Nexus FTIR spectrophotometer. The micro ATR accessory was a Harrick Split Pea with Si crystal. The detector used was a DTGS with KBr windows. The scan parameters for Forms I, II and the hydrate form were as follows:
number of scans: 32
resolution: 2 cm$^{-1}$
wavelength range: 4000 to 400 cm$^{-1}$
baseline correction: yes
beamsplitter: Ge on KBr.

The accuracy of the IR absorbance peaks provided for Forms I, II and the hydrated form is defined as 2 cm$^{-1}$ due to experimental differences, such as instrumentations, sample preparations, and the like.

The characterising differential scanning calorimetry (DSC) endothermic peak positions or ranges of Forms I and II are given in ° C.

Form I of compound (XIX) melts with decomposition. An exothermic signal is observed at about 216.8° C.

Form II of compound (XIX) melts with decomposition at about 197.3° C. An exothermic signal is observed at about 203.6° C. An extra endothermic signal in the DSC curve is observed at about 71.5° C. due to solvent evaporation.

Figure 3:
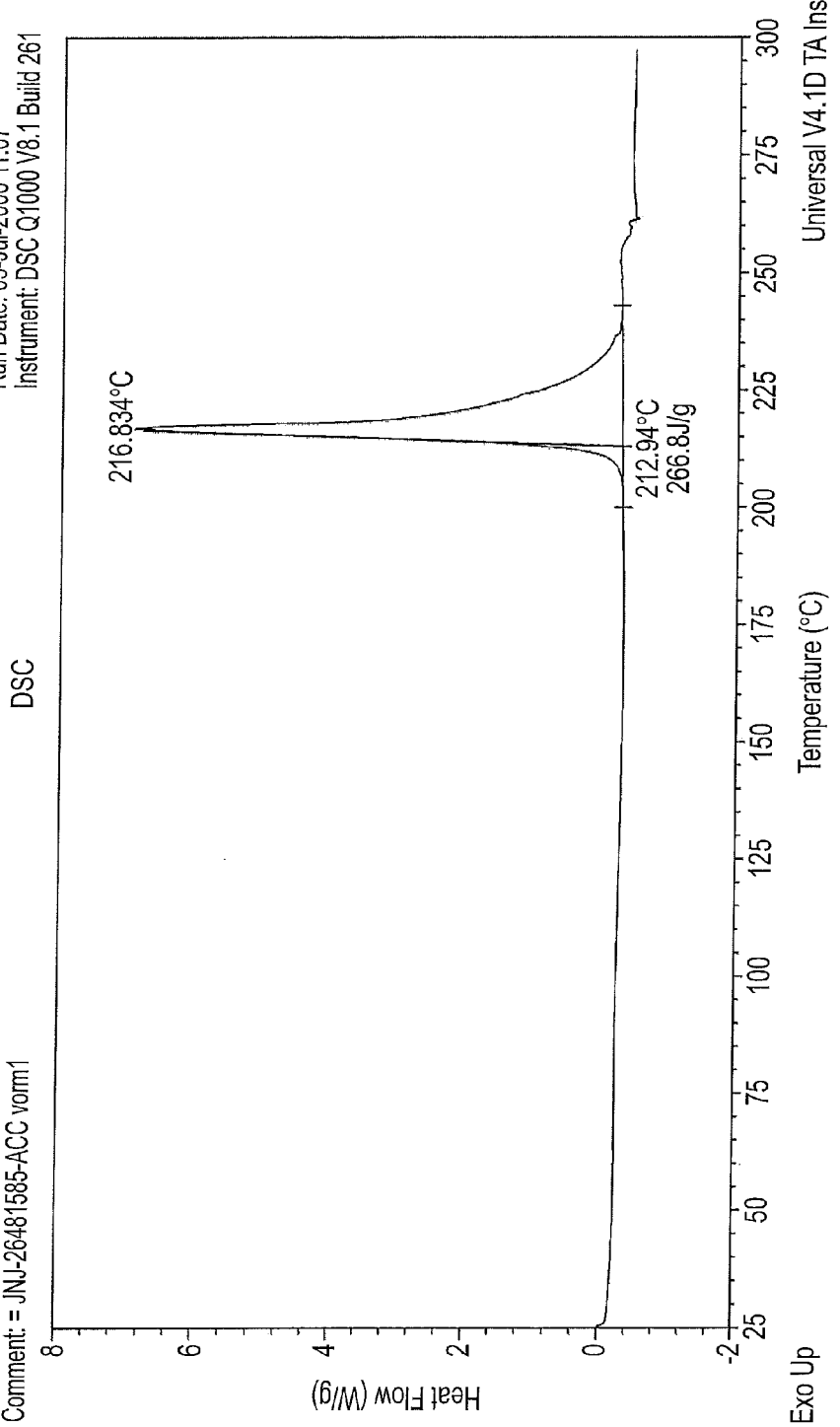
FIG. 3 is a Differential Scanning calorimetry (DSC) curve of Form I
Figure 8:
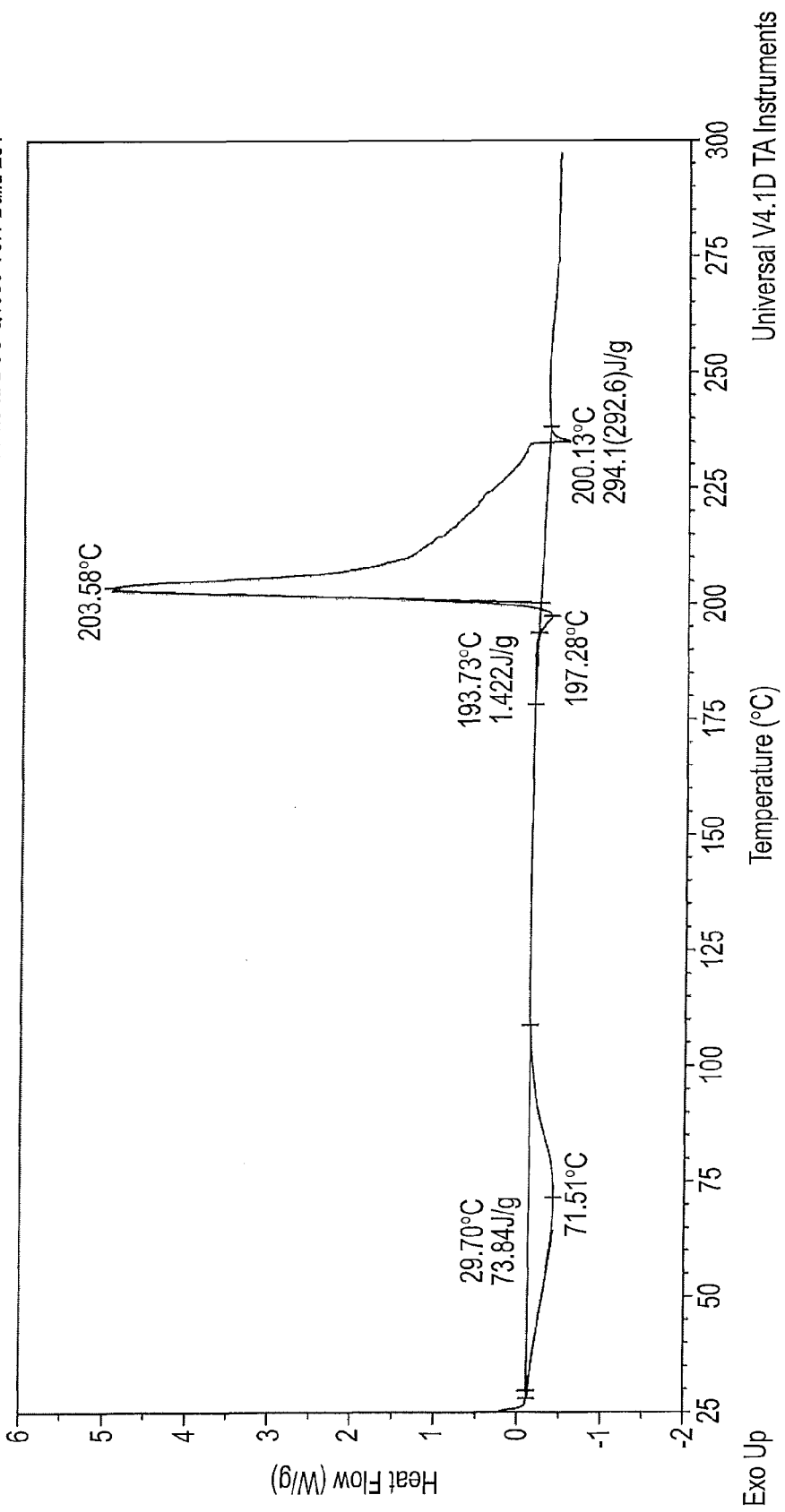
FIG. 8 is DSC curve of Form II

The DSC curve of Form I is as substantially depicted in FIG. 3. The DSC curve of Form II is as substantially depicted in FIG. 8.

The DSC data and curve representations were obtained using a TA-Instruments Q1000 MTDSC equipped with a RCS cooling unit. The weight of the samples was about 3 mg, which were transferred into a standard aluminum TA-Instrument sample pan. The samples were scanned at a rate of 10° C./min from 25° C. to a final temperature of 300° C. The oven was constantly purged with nitrogen gas at a flow rate of 50 ml/min.

The tolerance of the DSC curves provided for Forms I and II is defined as 3° C. due to experimental differences, such as instrumentations, sample preparations, and the like. The adsorption-desorption characteristics of Form I and Form II are given as % change in Mass.

Form I of compound (XIX) adsorbs up to 0.6% water at high relative humidity, it shows no hygroscopic behavior and remains crystalline during the test.

Form II of compound (XIX) is a hygroscopic product. It adsorbs up to 9.6% water at high relative humidity. The product dries completely during the desorption cycle and remains crystalline during the test.

Figure 5:
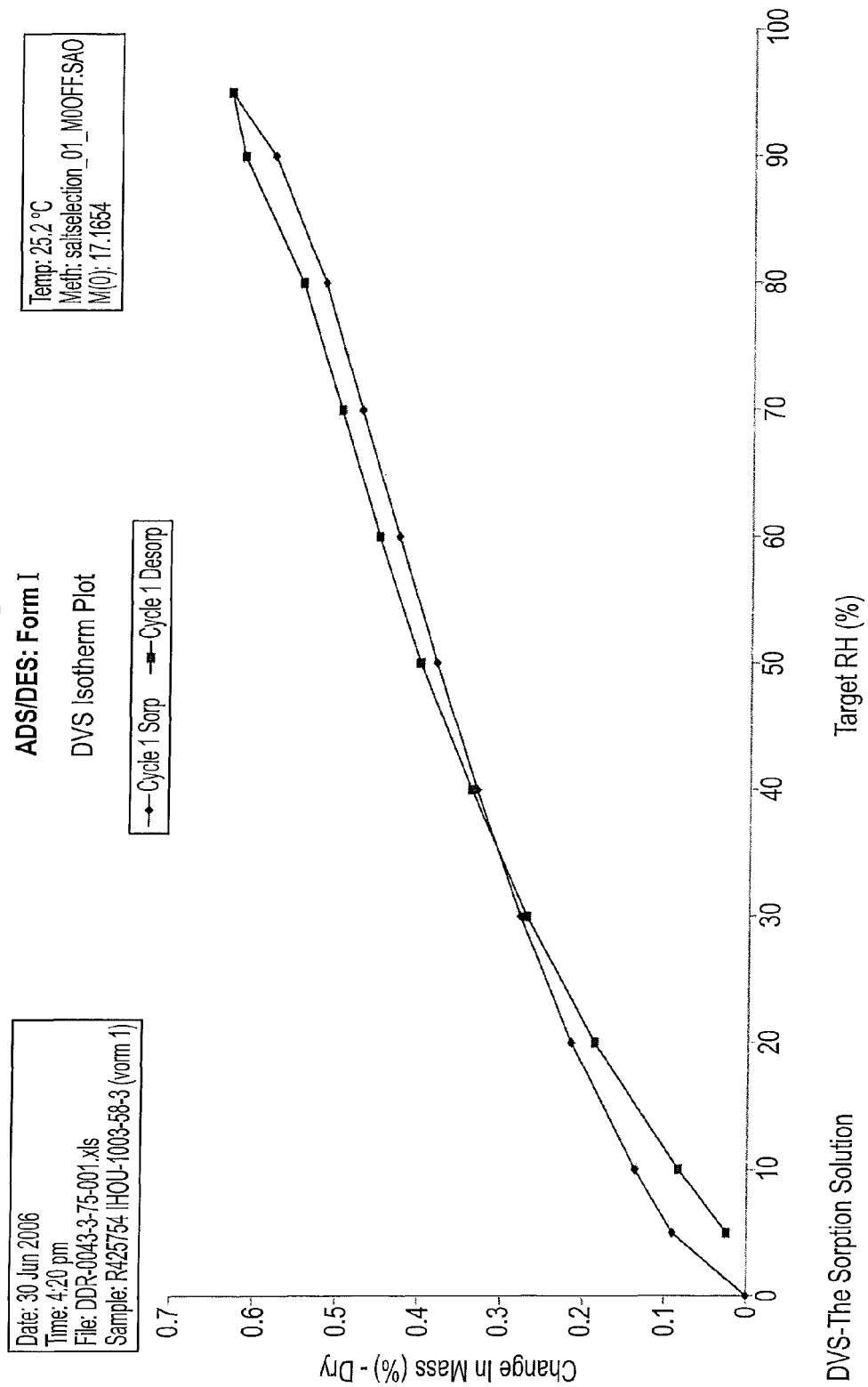
FIG. 5 is adsorption-desorption (ADS/DES) curve representation of Form I
Figure 10:
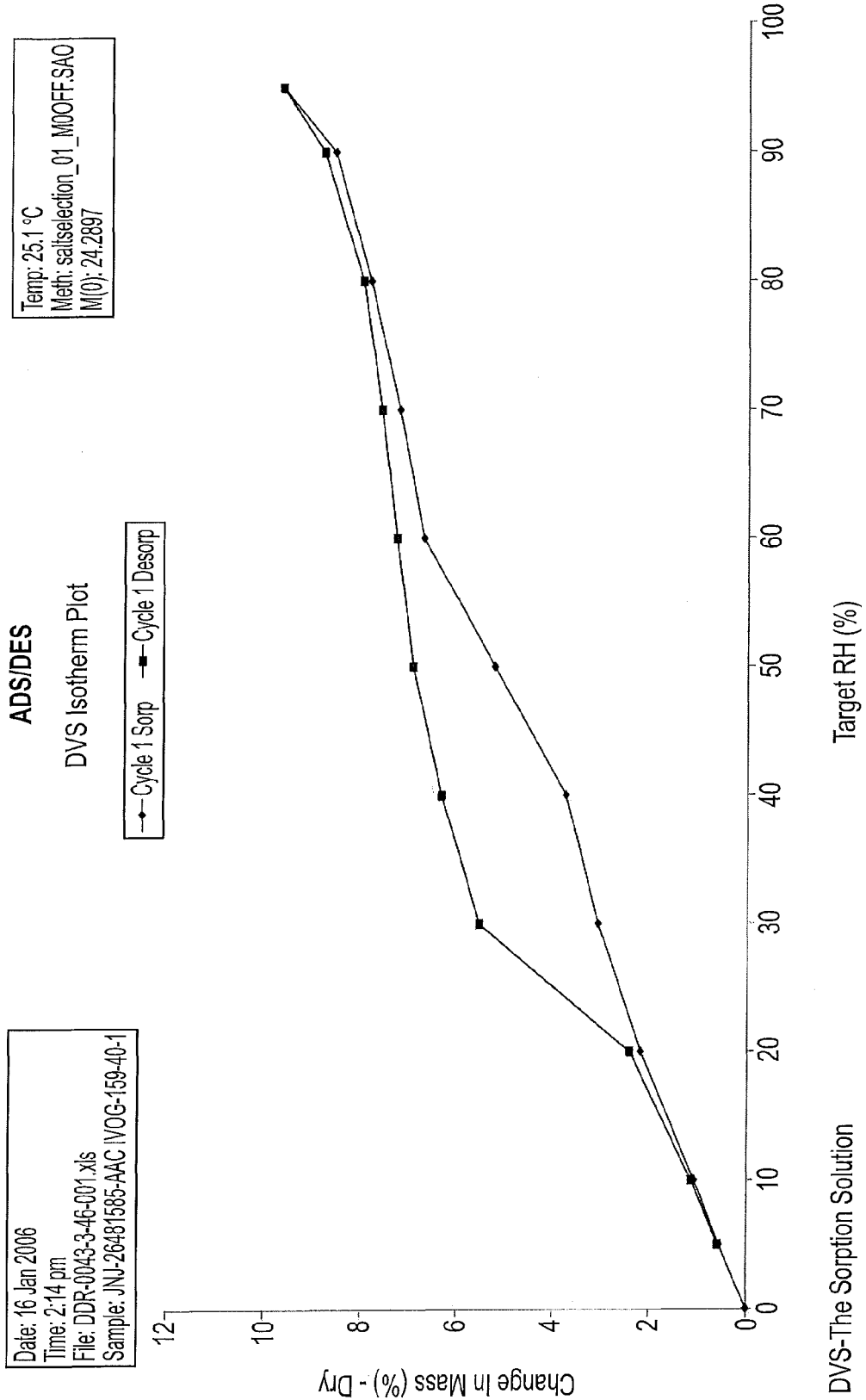
FIG. 10 is an ADS/DES curve representation of Form II

The ADS/DES curve of Form I is as substantially depicted in FIG. 5. The ADS/DES curve of Form II is as substantially depicted in FIG. 10.

The ADS/DES data were obtained using a SMS dynamic vapor sorption model DVS-1 and the weight change was recorded with tespect to the atmospheric humidity at 25° C. The weight of the samples was about 17 mg of Form I and 24 mg of Form II. The samples were dried for 60 min under dry nitrogen. The equilibrium was lower or equal to 0.01%/min. for minimal 15 min and maximal 60 min. The data interval was 0.05% or 2.0 min.
Relative Humidity (%) measurement points were:
first set: 5, 10, 20, 30, 40, 50, 60, 70, 80, 90, 95, 90, 80, 70, 60, 50, 40, 30, 20, 10, 5
second set: 5, 10, 20, 30, 40, 50, 60, 70, 80, 90, 95, 90, 80, 70, 60, 50, 40, 30, 20, 10, 5, 0.
Pharmaceutical Use of the Crystalline Forms The present invention further provides Form I, Form II or the hydrate form of the compound of formula (XIX), a mixture of two or more crystalline forms of the compound of formula (XIX), or a mixture of at least Form I or the hydrate form of the compound of formula (XIX) and the amorphous form of a non-HCl salt of the compound of formula (XIX), for use as a medicament. In one embodiment, the crystalline form, alone or in any of the above mixtures, for use as a medicament, is selected from Form I, Form II or the hydrated form.

The present invention further provides the use of at least Form I, Form II or the hydrate form of the compound of formula (XIX), a mixture of two or more crystalline forms of the compound of formula (XIX), or a mixture of at least Form I or the hydrate form of the compound of formula (XIX) and the amorphous form of a non-HCl salt of the compound of formula (XIX), in the manufacture of a medicament for the treatment of HDAC related conditions. In one embodiment, the crystalline form, alone or in any of the above mixtures, used in the manufacture of a medicament is selected from Form I, Form II and the hydrate form.

The present invention provides as well a method of treating a mammal suffering from HDAC-related conditions comprising administering at least Form I, Form II or the hydrate form of the compound of formula (XIX), a mixture of two or more crystalline forms of the compound of formula (XIX), or a mixture of at least Form I or the hydrate form of the compound of formula (XIX) and the amorphous form of a non-HCl salt of the compound of formula (XIX), to the mammal in need thereof. In one embodiment, the method of treatment comprises administering a crystalline form, alone or in any of the above mixtures, selected from Form I, Form II and the hydrate form.

As used herein, the terms "histone deacetylase" and "HDAC" are intended to refer to any one of a family of enzymes that remove acetyl groups from the ϵ-amino groups of lysine residues at the N-terminus of a histone.

Unless otherwise indicated by context, the term "histone" is meant to refer to any histone protein, including H1, H2A, H2B, H3, H4, and H5, from any species. Human HDAC proteins or gene products, include, but are not limited to, HDAC-1, HDAC-2, HDAC-3, HDAC-4, HDAC-5, HDAC-6, HDAC-7, HDAC-8, HDAC-9, HDAC-10 and HDAC-11. The histone deacetylase can also be derived from a protozoal or fungal source.

The term "treatment" refers to any treatment of a pathologic condition in a mammal, particularly a human, and includes one or more of the following acts:
(i) preventing the pathologic condition from occurring in a subject which may be predisposed to the condition but has not yet been diagnosed with the condition and, accordingly, the treatment constitutes prophylactic treatment for the disease condition;
(ii) inhibiting the pathologic condition, i.e., arresting its development;
(iii) relieving the pathologic condition, i.e., causing regression of the pathologic condition; or
(iv) relieving the symptoms mediated by the pathologic condition.

With the term "polymorph(s) of the present invention" is meant at least Form I, Form II or the hydrate form of the compound of formula (XIX), a mixture of two or more crystalline forms of the compound of formula (XIX), or a mixture of at least Form I or the hydrate form of the compound of formula (XIX) and the amorphous form of a non-HCl salt of the compound of formula (XIX).

This invention provides a method for inhibiting the abnormal growth of cells, including transformed cells, by administering an effective amount of a polymorph of the present invention. Abnormal growth of cells refers to cell growth independent of normal regulatory mechanisms (e.g. loss of contact inhibition). This includes the inhibition of tumour growth both directly by causing growth arrest, terminal differentiation and/or apoptosis of cancer cells, and indirectly, by inhibiting neovascularization of tumours.

This invention also provides a method for inhibiting tumour growth by administering an effective amount of a polymorph of the present invention, to a subject, e.g. a mammal (and more particularly a human) in need of such treatment. In particular, this invention provides a method for inhibiting the growth of tumours by the administration of an effective amount of a polymorph of the present invention. Examples of tumours which may be inhibited, but are not limited to, lung cancer (e.g. adenocarcinoma and including non-small cell lung cancer), pancreatic cancers (e.g. pancreatic carcinoma such as, for example exocrine pancreatic carcinoma), colon cancers (e.g. colorectal carcinomas, such as, for example, colon adenocarcinoma and colon adenoma), prostate cancer including the advanced disease, hematopoietic tumours of lymphoid lineage (e.g. acute lymphocytic leukemia, B-cell lymphoma, Burkitt's lymphoma), Hodgkins disease and non-Hodgkins disease, myeloid leukemias (for example, acute myelogenous leukemia (AML)), thyroid follicular cancer, myelodysplastic syndrome (MDS), tumours of mesenchymal origin (e.g. fibrosarcomas and rhabdomyosarcomas), melanomas, teratocarcinomas, neuroblastomas, gliomas, benign tumour of the skin (e.g. keratoacanthomas), breast carcinoma (e.g. advanced breast cancer), kidney carcinoma, ovary carcinoma, bladder carcinoma and epidermal carcinoma.

The present invention provides furthermore a pharmaceutical composition comprising at least Form I, Form II or the hydrate form of the compound of formula (XIX), a mixture of two or more crystalline forms of the compound of formula (XIX), or a mixture of at least Form I or the hydrate form of the compound of formula (XIX) and the amorphous form of a non-HCl salt of the compound of formula (XIX), and a pharmaceutically acceptable excipient. In one embodiment, the pharmaceutical composition comprises a crystalline form, alone or in any of the above mixtures, selected from Form I, Form II and the hydrate form.

Pharmaceutical compositions may be prepared as medicaments to be administered orally, parenterally (including subcutaneously, intramuscularly, and intravenously), rectally, transdermally, bucally, or nasally. Suitable forms for oral administration include powders, granulates, aggregates, tablets, compressed or coated pills, dragees, sachets, hard or gelatin capsules, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art. Although the most suitable administration in any given case will depend on the nature and severity of the condition being treated, the most preferred route of the present invention is oral.

The dosages may be conveniently presented in unit dosage form and prepared by any of the methods well-known in the pharmaceutical arts. Alternatively, the dosage forms may be presented as one, two, three or four or more subdoses administered at appropriate intervals throughout the day. The unit dosage used is preferably from about 1 mg to about 1000 mg of compound of formula (XIX) base equivalent, more preferably from about 5 to about 400 mg.

Pharmaceutical compositions of the present invention comprise Form I, Form II or the hydrate form of the compound of formula (XIX). The pharmaceutical composition may comprise only a single form of Form I, Form II or the hydrate form of the compound of formula (XIX), or a mixture of various forms of compound of formula (XIX), with or without amorphous forms of a non-HCl salt of the compound of formula (XIX). In addition to the active ingredient(s), the pharmaceutical composition comprises one or more excipients or adjuvants. Selection of excipients and the amounts to use may be readily determined by the galenist based upon experience and consideration of standard procedures and reference works in the field.

Examples of suitable excipients are gum arabic, magnesia, magnesium carbonate, potassium phosphate, lactose, glucose, or starch, in particular, corn starch. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the polymorphs of the present invention, if desired with the substances customary therefor such as solubilizers, emulsifiers or further auxiliaries, are brought into solution, suspension, or emulsion. The polymorphs of the present invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical compositions for administration in the form of aerosols or sprays are, for example, solutions, suspensions or emulsions of the polymorphs of the invention in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

It should be understood that in addition to the ingredients particularly mentioned above, the pharmaceutical compositions of the present invention may include other agents conventional in the art having regard to the type of formulation in question, for example those suitable for oral administration may include flavouring agents or taste masking agents.

As another aspect of the present invention, a combination of Form I, Form II or the hydrate form of the compound of formula (XIX), a mixture of two or more crystalline forms of the compound of formula (XIX), or a mixture of at least Form I or the hydrate form of the compound of formula (XIX) and the amorphous form of a non-HCl salt of the compound of formula (XIX), with another anticancer agent is envisaged, especially for use as a medicine, more specifically in the treatment of cancer or related diseases.

For the treatment of the above conditions, a polymorph of the present invention may be advantageously employed in combination with one or more other medicinal agents, more particularly, with other anti-cancer agents. Examples of anti-cancer agents include but are not limited to:

platinum coordination compounds for example cisplatin, carboplatin or oxalyplatin;

taxane compounds for example paclitaxel or docetaxel;

topoisomerase I inhibitors such as camptothecin compounds for example irinotecan or topotecan;

topoisomerase II inhibitors such as anti-tumour epipodophyllotoxins or podophyllotoxin derivatives for example etoposide or teniposide;

anti-tumour vinca alkaloids for example vinblastine, vincristine or vinorelbine;

anti-tumour nucleoside derivatives for example 5-fluorouracil, leucovorin, gemcitabine or capecitabine;

alkylating agents such as nitrogen mustard or nitrosourea for example cyclophosphamide, chlorambucil, carmustine, thiotepa, mephalan or lomustine;

anti-tumour anthracycline derivatives for example daunorubicin, doxorubicin, doxil, idarubicin or mitoxantrone;

molecules that target the IGF-1 receptor for example picropodophilin;

tetracarcin derivatives for example tetrocarcin A;

glucocorticoïden for example prednisone;

antibodies for example trastuzumab (HER2 antibody), rituximab (CD20 antibody), gemtuzamab, cetuximab, pertuzumab or bevacizumab;

estrogen receptor antagonists or selective estrogen receptor modulators for example tamoxifen, fulvestrant, toremifene, droloxifene, faslodex or raloxifene;

aromatase inhibitors such as exemestane, anastrozole, letrazole and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, caminomycin or daunomycin;

antimetabolites for example chlofarabine, aminopterin, cytosine arabinoside or methotrexate;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors for example flavoperidol, imatinib mesylate, erlotinib or gefitinib;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585 or trichostatin A;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

In view of their useful pharmacological properties, the components of the combinations according to the invention, i.e. the other medicinal agent and the polymorphs of the invention, may be formulated into various pharmaceutical forms for administration purposes. The components may be formulated separately in individual pharmaceutical compositions or in a unitary pharmaceutical composition containing both components.

One embodiment of the present invention therefore also relates to a pharmaceutical composition comprising the other medicinal agent and the polymorphs of the present invention together with one or more pharmaceutical carriers.

The present invention further relates to the use of a combination according to the invention in the manufacture of a pharmaceutical composition for inhibiting the growth of tumour cells.

The present invention further relates to a product containing as first active ingredient a polymorph according to the invention and as second active ingredient an anticancer agent, as a combined preparation for simultaneous, separate or sequential use in the treatment of patients suffering from cancer.

The other medicinal agent and the polymorph of the invention may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and the polymorph being administered, their route of administration, the particular tumour being treated and the particular host being treated. The optimum method and order of administration and the dosage amounts and regime can be readily determined by those skilled in the art using conventional methods and in view of the information set out herein.

The platinum coordination compound is advantageously administered in a dosage of 1 to 500 mg per square meter $(mg/m^2)$ of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter $(mg/m^2)$ of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter $(mg/m^2)$ of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter $(mg/m^2)$ of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter $(mg/m^2)$ of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter $(mg/m^2)$ of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter $(mg/m^2)$ of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

It may be convenient to store the polymorphs of the invention in packaging materials which are protective to mechanical, environmental, biological or chemical hazards, or degradation. Conditioning drug substances can be achieved by employing packaging materials impermeable to moisture, such as sealed vapour lock bags. Conditioning drug products, such as tablets, capsules, can be achieved by employing for instance, aluminium blisters.

EXPERIMENTAL PART

The following examples are intended to illustrate the present invention and not to limit it thereto.

Example 1

Preparation of Intermediate (I)

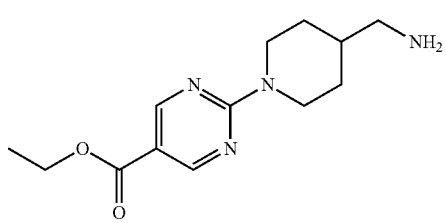

a) 4-piperidinemethanamine (2.6 mol) and ethyl acetate (5.2 L) was brought in an inert reactor (20 L) and warmed up to 45° C. 4-nitrobenzaldehyde (2.7 mol) was added and the reaction mixture was stirred for 2 h at 45° C. The reaction was cooled to 0° C. and then diisopropylethylamine (6.6 mol) was added giving solution 1.

b) 2-(methylthio)-5-pyrimidinecarboxylic acid ethyl ester (2.7 mol) and ethyl acetate (2.6 L) was brought in an inert reactor and cooled to 0° C. A solution of meta-chloroperoxy benzoic acid (1.2 mol) in ethyl acetate (2.6 L) was added over a time period of 1 h at a temperature between 0° C. and 5° C. The reaction mixture was stirred for 30 min at 0° C. giving solution 2.

c) Solution 2 was added to solution 1 over a time period of 1 h at a temperature between 0° C. and 5° C. The reaction mixture was left overnight at room temperature. The mixture was acidified to a pH of 2, with a solution of 640 ml concentrated hydrochloric acid in 10 L water. The aqueous layer was collected and washed with 1 L ethyl acetate. The aqueous layer was collected and 1 L of dichloromethane was added. The mixture was basified to a pH of 10, with 450 ml sodium hydroxide 50%. The mixture was stirred for 30 min at room temperature. The organic layer was collected giving fraction 1. The aqueous layer was further extrated with 2 L dichloromethane and the organic layer was collected giving fraction 2. Fraction 1 and 2 were combined and dichloromethane was evaporated giving 511.25 g (1.93 mol) of intermediate (I) (yield 74%).

Example 2

Preparation of Intermediate (XIII)

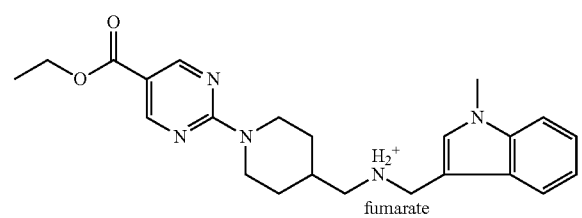

a) Intermediate (I) (0.97 mol), and toluene (4.5 L) was added in an inert reactor (20 L). 1-methyl-1H-Indole-3-carboxaldehyde (0.97 mol) was added to the reaction mixture at room temperature. The reaction mixture was warmed to reflux temperature, refluxed overnight and cooled to room temperature. Ethanol (1.5 L) degenerated with methanol was added giving solution 3.

b) Sodium tetrahydroborate (55.2 g) and toluene (1.5 L) was added in an inert reactor (20 L). The mixture was brought to 10° C. under continuous stirring. Solution 3 was added to the mixture over a time period of 1 h at a temperature #10° C. The mixture was stirred for 1 h at a temperature #10° C. The reaction mixture was brought at room temperature. Acetone (8.79 mol) was added over a time period of 30 min. The reactionmixture was stirred for 4 h. Water (5.1 L) was dripped to the reaction mixture over a time period of 15 min. The reaction mixture was stirred for 1 h at room temperature. The aqueous layer was disregarded and the organic layer was washed two times with a solution of 300 g sodium bicarbonate in 4.1 L water. The organic layer was filtered over magnesium sulfate and evaporated giving fraction 3 (397 g of residue after evaporation).

c) Ethanol (5 L) degenerated with 2% methylethylketone is added to fraction 3 at room temperature. Concentrated acetone (5 L) and 0.5 L water is added at room temperature and the mixture is subsequently warmed to 50° C. A mixture of fumaric acid (0.97 mol), ethanol (1.4 L) degenerated with 2% methylethylketone, acetone (1.4 L) and 140 ml water was prepared giving solution 4. Solution 4 was added to the reaction mixture over a time period of 2 h at a temperature of 50° C. The reaction mixture was stirred for 2 h at 50° C., cooled for 4 h to room temperature and stirred overnight at room temperature. The sediment was collected and was subsequently washed with 1.4 L ethanol degenerated with 2% methylethylketone, 1.4 L concentrated acetone and 140 ml of water. The sediment was dryed overnight at 50° C., giving 371 g (0.7 mol) of intermediate (XIII) (yield 73%).

Example 3

Preparation of Intermediate (XVII)

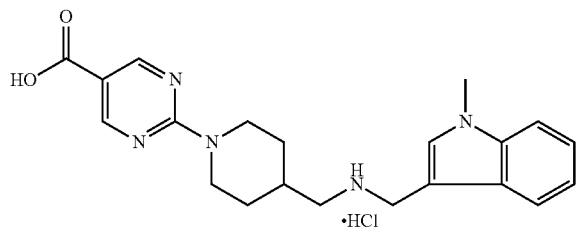

(XVII)

Al four necked flask (2 L) was charged with intermediate (XIII) (100 g; 191.0 mmoles). Water (3 L/mol-pure limiting reagent; 573.0 ml) and 2-methyltetrahydrofuran (2.2 L/mol-pure-limiting reagent; 420.2 ml) was added. After stirring, sodium hydroxide 50% (2.5 moles/mol-pure-limiting reagent; 477.5 mmoles; 25.13 ml) was added. The reaction mixture was further stirred for 40-60 min at room temperature, whereafter the reaction was left to settle. The upper organic layer was collected and washed with water (2 L/mol-pure-limiting reagent; 382.0 ml). Water (1.5 L/mol-pure-limiting reagent; 286.5 ml) and sodium hydroxide (3 moles/mol-pure-limiting reagent; 573.0 mmoles; 45.84 g) were added to the organic layer. The reaction mixture was warmed to 80° C. and stirred during 16 h. The reaction mixture was cooled to room temperature and the lower water layer was collected. Isopropyl alcohol (90 ml; 1.177 moles) was added and the mixture was cooled to 10° C. in an ice bath. The reaction mixture was acidified with concentrated hydrochloric acid (5 moles/mol-pure-limiting reagent; 954.9 mmoles; 100.9 g) to pH 1 (pH 13.8: darkgreen solution; pH 7.5 oldpink solution; pH 4.7: pink solution, white precipitate). The reaction mixture was stirred for 4 h at 10° C. The white precipitate was filtered, washed 4 times with water and dryed under vacuum at 40° C. giving 84 g intermediate (XVII) (yield: 97%).

Example 4

Preparation of Intermediate (XVIII)

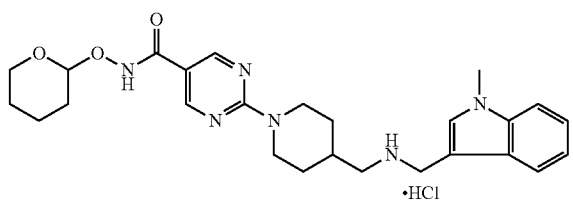

(XVIII)

a) A four-necked flask (1 L) was charged with 0.093 mol of intermediate (XVII) and 220 ml of ethyl acetate was added. The reaction mixture was stirred and 5 ml of water was added giving solution 5. A 250 ml flask was charged with 0.122 mol of N'-(ethylcarbonimidoyl)-N,N-dimethyl-1,3-propanediamine, monohydrochloride (EDC) in 130 ml of ethanol and the reactionmixture was stirred giving solution 6. O-(tetrahydro-2H-pyran-2-yl)-hydroxylamine (0.123 mol) was added to solution 5 and the addition funnel was washed with 26 ml of ethyl acetate. Immediately thereafter 200 ml of solution 6 was added to the reaction mixture comprising solution 5 over a time period of 1 h 30 min (the reaction mixture became homogeneous when 90% of solution 6 was added, then the desired product crystallized out). The reaction mixture was stirred at room temperature for 5 h. The precipitate was filtered and washed with 55 ml ethyl acetate and dryed under vacuum at 50° C. during 16 h, giving 35.7 g (0.07 mol) of intermediate (XVIII) (yield: 71%).

b) A four-necked flask (1 L) was charged with 0.073 mol of intermediate (XVIII) under nitrogen atmosphere. N,N dimethyl acetamide (377 ml) and 377 ml methylisobutylketone were added and the mixture was warmed to 70° C. The reaction mixture was stirred for 5 h at 70° C., then cooled down over a time period of 1 h to 25° C. and then stirred for another hour at 25° C. The precipitate was filtered and subsequently washed with 94 ml of a mixture of N,N dimethyl acetamide and methylisobutylketone, then 150 ml of methylisobutylketone in a slurry wash and then 150 ml of methylisobutylketone in a displacement wash. The precipitate was dryed under vacuum at 50° C. during 2 days giving 33.4 g of purified intermediate (XVIII) (yield: 89%).

Example 5

Preparation of JNJ-26481585 HCl Salt Crystal Form I

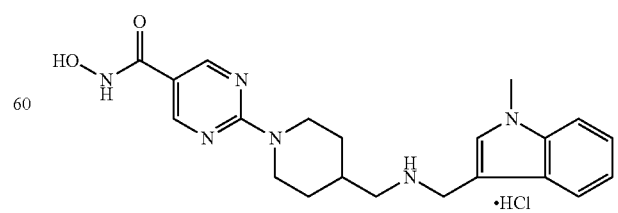

JNJ-26481585 HCl salt crystal form I a) An inert four-necked flask (0.5 L) was charged with 0.03 mol of purified intermediate (XVIII). Ethanol (300 ml) was added (typical water content is 0.07% (w/w)). The reaction mixture was stirred and warmed to 57° C.-60° C. 30 mg of intermediate (XVIII) JNJ-26481585.HCl (30 mg) Form I was seeded. Concentrated hydrochloric acid (0.05 mol %) was added to the reaction mixture at 57° C. and the reaction mixture was stirred during 16 h. The precipitate was filtered at 50° C. and washed 3 times with 20 ml of ethanol giving 10 g JNJ-26481585 HCl salt crystal Form I.

b) An inert four-necked flask (50 ml) was charged with 2.6 g of JNJ-26481585 HCl salt crystal Form I obtained in step a). Ethanol (20 ml) was added. The reaction mixture was stirred under nitrogen and in the dark and warmed to 50° C. The reaction mixture was stirred during 12 h at 50° C., cooled to 40° C. over a time period of 1 h and filtered. The precipitate was washed one time with 20 ml ethanol and two times with 20 ml acetone. Then the product was dried at 50° C. under vacuum for 16 h yielding 2 g (80%) of purified JNJ-26481585 HCl salt crystal Form I.

Example 6

Transformation of a Mixture of Polymorph I and II Using a Slurry Procedure a) Preparation of the Slurries About 25 mg of Form I and about 25 mg of Form II were weighted in a vial. About 0.2 ml ethanol was added and the vial was closed. Three vials were prepared and each vial was stored for 4 days at a different temperature, at 4° C. (refrigerator), 40° C. and 70° C.

This was repeated for the slurries in ethanol/water (90/10, v/v %) and in water.

The slurries were stored for 4 days and 7 days at the different temperatures.

After storage the vial was opened and the sample was dryed by spreading a few mg of the slurry on a paper filter.

b) Analytical Techniques (Powder XRD)

All obtained fractions were analyzed using powder XRD.

X-ray powder diffraction (XRPD) analyses were carried out on a Philips X'PertPRO MPD diffractometer PW3050/60 with generator PW3040. The instrument was equipped with a Cu LFF X-ray tube PW3373/00.

The compound was spread on a zero background sample holder.

Instrument Parameters
 generator voltage: 45 kV
 generator amperage: 40 mA
 geometry: Bragg-Brentano
 stage: spinner stage
Measurement Conditions
 scan mode: continuous
 scan range: 3 to 50° 2θ
 step size: 0.01675°/step
 counting time: 29.85 sec/step
 spinner revolution time: 1 sec
 radiation type: CuKα
 radiation wavelength: 1.54056 Å

| Incident beam path | | Diffracted beam path | |
|---|---|---|---|
| program. divergence slit: | 15 mm | long anti scatter shield: | + |
| Soller slit: | 0.04 rad | Soller slit: | 0.04 rad |

| Incident beam path | | Diffracted beam path | |
|---|---|---|---|
| beam mask: | 15 mm | Ni filter: | + |
| anti scatter slit: | 1° | detector: | X'Celerator |
| beam knife: | + | | | c) Results

The results obtained in the slurry conversion studies after 4 days and 7 days storage in ethanol were collected in the following Table A.

| Slurry Time and Temperature | after 4 days ethanol | after 7 days ethanol |
|---|---|---|
| 4° C. refrigerator | Mixture of Solvate + Form I + Form II | Mixture of Solvate + Form I |
| 40° C. | Mixture of Form I + Form II (*) | Mixture of Solvate + Form I |
| 70° C. | Form I | Form II |

The XRD pattern of the solvated form is comparable to the XRD pattern of the Hydrate The results obtained in the slurry conversion studies after 4 days and 7 days storage in ethanol/water (90/10, v/v %) are collected in the following Table B.

| Slurry Time and Temperature | after 4 days ethanol/water (90/10, v/v %) | after 7 days ethanol/water (90/10, v/v %) |
|---|---|---|
| 4° C. refrigerator | Mixture of Hydrate + Form I | Mixture of Hydrate + Form I |
| 40° C. | Mixture of Form I + Form II (*) | Mixture of Hydrate + Form I |
| 70° C. | Mixture of Hydrate + Form I | Form I + traces of Hydrate |

(*) The solvent present in the slurry was completely evaporated. After four days storage again 0.2 ml solvent was added to the mixture.

The results obtained in the slurry conversion studies after 4 days storage in water are collected in the following Table C.

| Slurry Time and Temperature | after 4 days water |
|---|---|
| 4° C. refrigerator | Hydrate |
| 40° C. | Hydrate |
| 70° C. | Hydrate |

These hydrated samples (ex slurries in water) were stored for 3 days with 0.1 ml ethanol at different temperatures, 40° C., 50° C. and 70° C.

The hydrated samples stored for 3 days at 40° C. and 50° C. remained hydrate.

The hydrated sample stored for 3 days at 70° C. was completely liquefied (oil).

Example 7

Stability of Form I a) Compound Information
Graphic Formula:

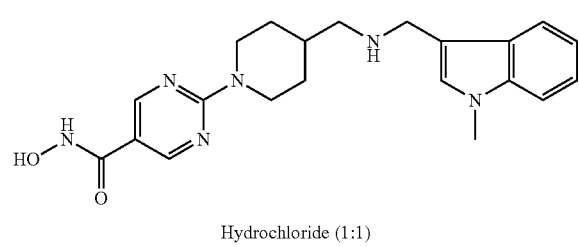 [SMILES: Cn1cc(CNCC2CCN(c3ncc(C(=O)NO)cn3)CC2)c2ccccc21]

Hydrochloride (1:1)

Chemical name: N-hydroxy-2-[4-[[[(1-methyl-1H-indol-3-yl)methyl]amino]methyl]-1-piperidinyl]-5-pyrimidinecarboxamide hydrochloride Molecular formula: $C_{21}H_{26}N_6O_2 \cdot HCl$
Molecular weight: 430.94 b) Adsorption/Desorption Study

The adsorption and desorption of water at 25° C. at different conditions of relative humidity was investigated on 17 mg Form I.

The weight change as a function of relative humidity was registered.

Figure 4:
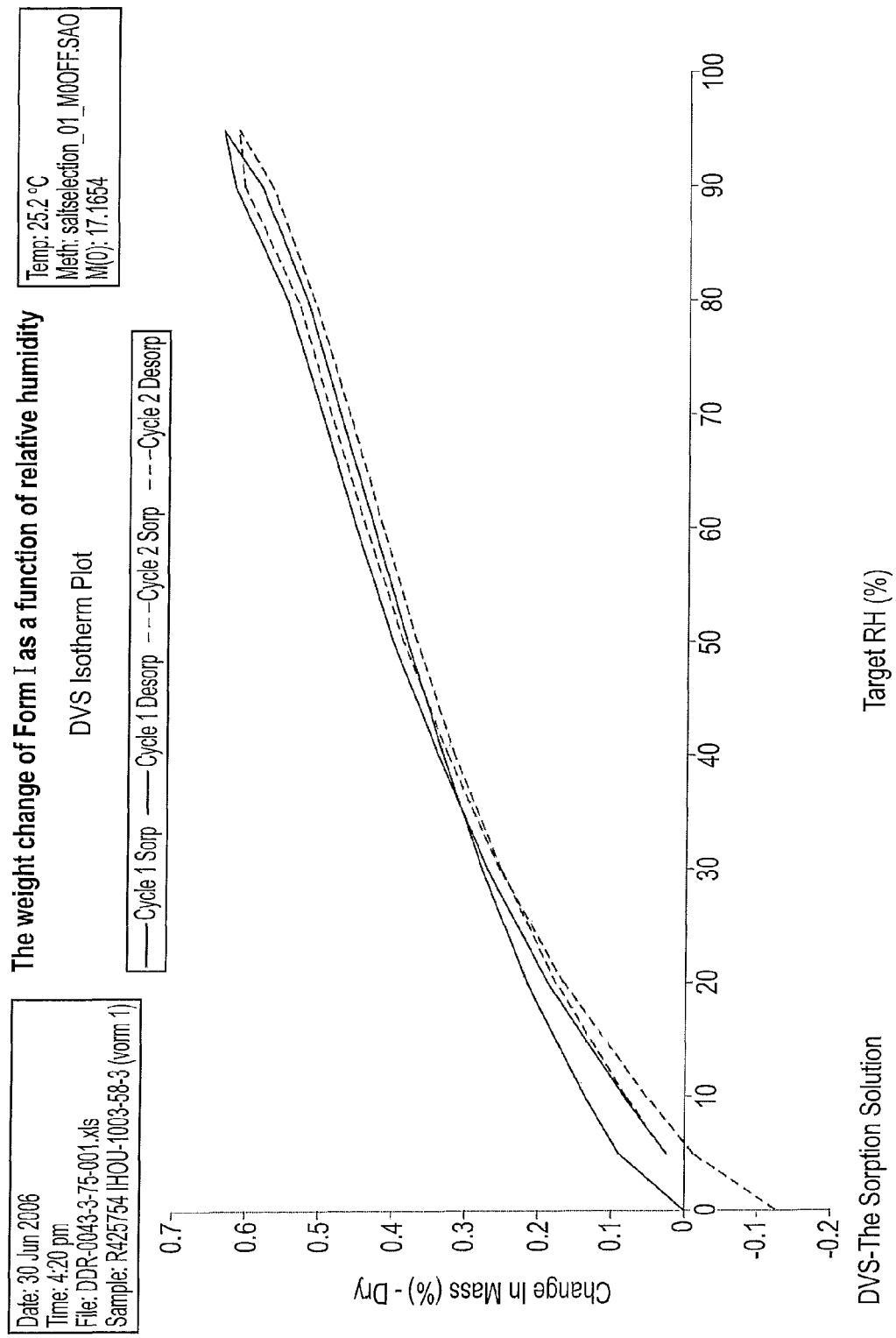
FIG. 4 is the weight change of Form I as a function of relative humidity

The result were displayed in the FIG. 4.

Form I fraction adsorbs up to 0.6% water at high relative humidity, it showed no hygroscopic behavior and remained crystalline during the test.

c) Solubility

Aqueous solubilities of Form I were measured in solvents with different pH. An excess of the solute was equilibrated with the solvent at 20° C. for 24 hours. After removing the undissolved compound, the concentration in solution was determined using UV spectrometry.

The solubilities were listed in the following Table D:

| Solvent Form I | Solubility (mg/ml solution) | |
|---|---|---|
| water | 1.4 | (pH 4.5) |
| 0.01N HCl | 1.4 | (pH 2.0) |
| 0.001N HCl | 1.5 | (pH 2.9) |
| Buffer pH 2 (citric acid/NaOH/HCl) | 0.95 | (pH 2.0) |
| Buffer pH 4 (citric acid/HCl/NaOH) | 1.2 | (pH 3.9) |
| Buffer pH 6 (citric acid/NaOH) | 1.5 | (pH 6.0) |
| Buffer pH 8 (boric acid/HCl/NaOH) | 1.3 | (pH 7.8) |
| Buffer pH 10 (boric acid/KCl/NaOH) | 1.3 | (pH 9.8) | d) Crystallographic Stability

The stability of the crystal structure of Form I was studied after storage of the compound in open conditions for a period of six weeks at room temperature (RT) under <5%, 56% and 75% relative humidity (RH), 50° C. and 40° C./75% RH.

The samples are analyzed with thermogravimetry (TGA), differential scanning calorimetry (DSC), X-ray powder diffraction (XRPD) and infrared spectroscopy (IR).

The results of the tests are reported in the following table E.

| product | | TGA | | | | DSC Exotherm | |
|---|---|---|---|---|---|---|---|
| Form I | condition | <100° C. | <200° C. | XRD | IR | Max (° C.) | App |
| •HCl | 0 days | 0.4 | 0.9 | Cryst., Ref | Cryst., Ref | 216.8 | Beige-gray |
| | RT/<5% RH | 0.8 | 0.5 | ~Ref | ~Ref | 216.7 | Beige-gray |
| | RT/56% RH | 0.5 | 0.4 | ~Ref | ~Ref | 216.9 | Beige-gray |
| | RT/75% RH | 0.9 | 0.4 | ~Ref | ~Ref | 217.0 | Beige-gray |
| | 50° C. | 0.5 | 0.3 | ~Ref | ~Ref | 216.9 | Beige-gray |
| | 40° C./75% RH | 1.0 | 0.3 | ~Ref | ~Ref | 216.9 | Beige-gray |

~Ref: identical with reference
Cryst.: crystalline

Form I melted with decomposition, therefore no heat of fusion was reported.

Form I is crystallographically stable.

No changes are observed after storage under the different conditions.

The IR spectra, XRD patterns and the DSC curves remain the same before and after storage.

e) Chemical Stability

Form I was stored in different open conditions for periods of 1, 4 and 8 weeks.

These conditions are 40° C./75% RH, 50° C., RT/<5% RH, RT/56% RH, RT/75% RH and 0.3 da ICH light.

The compounds were analyzed after storage by HPLC and by visual inspection.

The results of the tests were reported in the following table F.

| | | HPLC Sum of impurities | | | Appearance | | |
|---|---|---|---|---|---|---|---|
| product | condition | 1 week | 4 weeks | 8 weeks | 1 week | 4 weeks | 8 weeks |
| Form I HCl salt | Reference | 3.14 | — | — | beige-gray | — | — |
| | 0.3 da ICH light | 4.58 | — | — | beige-gray | — | — |
| | 40° C./75% RH | 3.31 | 3.13 | 3.59 | beige-gray | beige-gray | beige-gray |
| | 50° C. | 3.19 | 3.20 | 3.16 | beige-gray | beige-gray | beige-gray |
| | RT/<5% RH | — | 3.42 | 3.16 | — | beige-gray | beige-gray |
| | RT/56% RH | — | 3.27 | 3.15 | — | beige-gray | beige-gray |
| | RT/75% RH | — | 3.43 | 3.39 | — | beige-gray | beige-gray |

Form I showed a sensitivity towards light, as the sum of impurities increased after storage in 0.3 da ICH light conditions.

Example 8

Stability of Form II a) Compound Information
Graphic Formula:

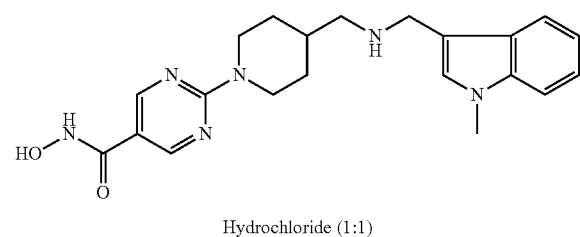 [SMILES: Cn1cc(CNCC2CCN(c3ncc(C(=O)NO)cn3)CC2)c2ccccc21]

Hydrochloride (1:1)

Chemical name: N-hydroxy-2-[4-[[[(1-methyl-1H-indol-3-yl)methyl]amino]methyl]-1-piperidinyl]-5-pyrimidinecarboxamide hydrochloride Molecular formula: $C_{21}H_{26}N_6O_2 \cdot HCl$
Molecular weight: 430.94 b) Adsorption/Desorption Study

The adsorption and desorption of water at 25° C. at different conditions of relative humidity was investigated on about 24 mg Form II The weight change as a function of relative humidity was registered.

Figure 9:
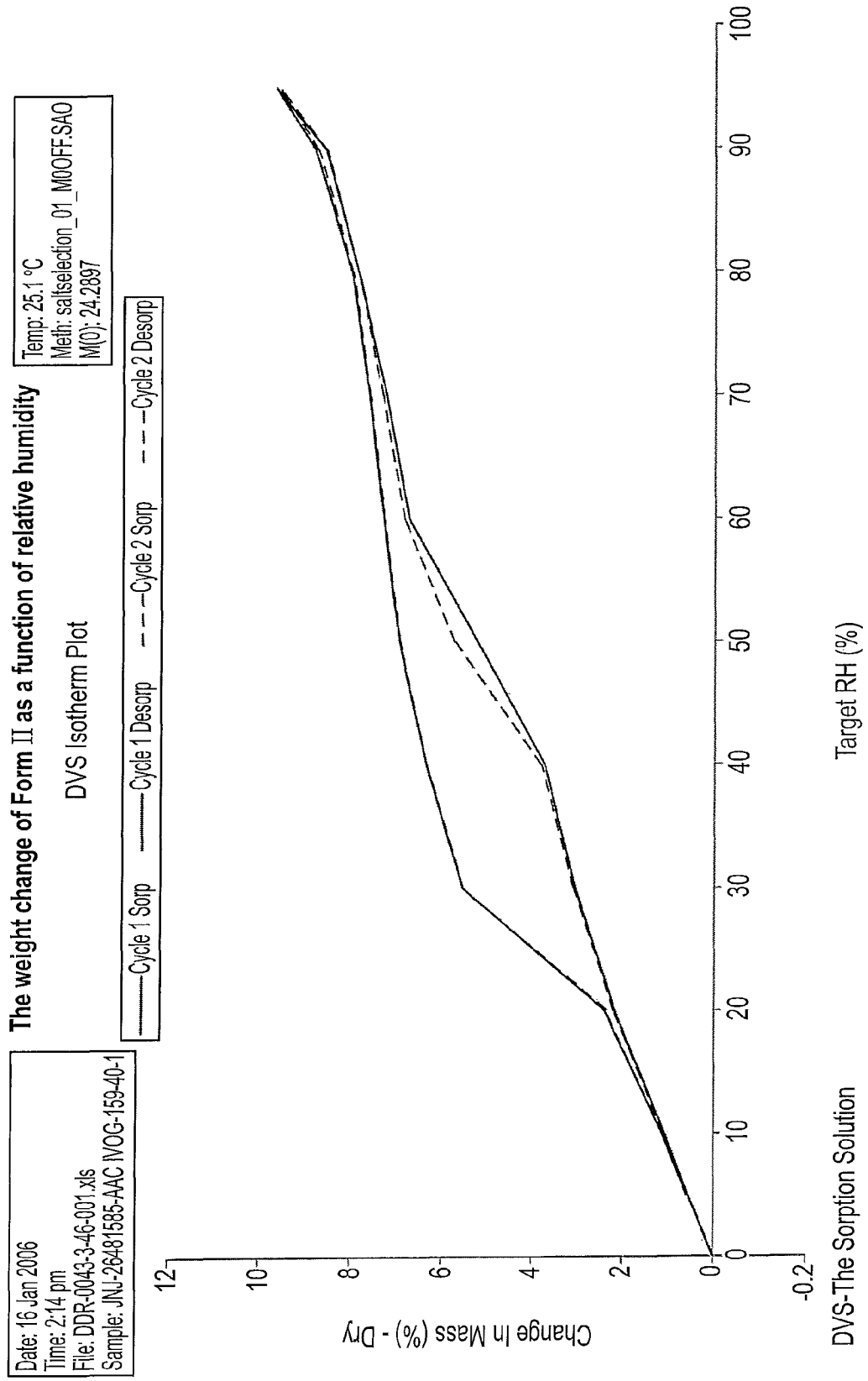
FIG. 9 is the weight change of Form II as a function of relative humidity

The result were displayed in the FIG. 9.

During the initial drying step a weight loss of 1.67% is registered for Form II. The obtained dried product was hygroscopic. It adsorbed up to 9.6% water at high relative humidity.

The product dryed completely during the desorption cycle and remained crystalline during the test.

c) Crystallographic Stability

The stability of the crystal structure of Form II was studied after storage of the compound in open conditions for a period of six weeks at room temperature (RT) under <5%, 56% and 75% relative humidity (RH), 50° C. and 40° C./75% RH.

The samples were analyzed with thermogravimetry (TGA), differential scanning calorimetry (DSC), X-ray powder diffraction (XRPD) and infrared spectroscopy (IR).

The results of the tests were reported in the following table G.

| | | TGA | | | | DSC | | |
|---|---|---|---|---|---|---|---|---|
| product | condition | <100° C. | <170° C. | XRD | IR | Extra (° C.) | Max (° C.) | App |
| •HCl salt | 0 days | 3.3 | 0.4 | Cryst., Ref | Cryst., Ref | 71.5 (78 J/g) | ±198 | white |
| | RT/<5% RH | 1.9 | 0.4 | ~Ref | ~Ref | 75.1 (68 J/g) | ±198 | white |
| | RT/56% RH | 5.2 | 0.3 | ≠Ref | ≠Ref | 87.1 (144 J/g) | ±198 | slightly pink |
| | RT/75% RH | 4.9 | 0.3 | ≠Ref | ≠Ref | 85.2 (153 J/g) | ±198 | slightly pink |
| | 50° C. | 2.1 | 0.2 | ~Ref | ~Ref | 74.6 (66 J/g) | ±198 | white |
| | 40° C./75% RH | 6.0 | 0.2 | ≠Ref | ≠Ref | 83.9 (151 J/g) | ±198 | pink |

~Ref: identical with reference
Cryst.: crystalline

Form II melted with decomposition, therefore no heat of fusion was reported. The extra endothermic signal in the DSC curve was due to solvent evaporation.

Form II is crystallographically not stable.

Changes are observed after storage under the different humid conditions. The IR spectra and XRD patterns are different from the starting material after storage under RT/56% RH, RT/75% RH and 40° C./75% RH condition.

The changes after storage under RT/56% RH, RT/75% RH and 40° C./75% RH condition were due to the uptake of water.

d) Chemical Stability

Form II was stored in different open conditions for periods of 1, 4 and 8 weeks. These conditions were 40° C./75% RH, 50° C., RT/<5% RH, RT/56% RH, RT/75% RH and 0.3 da ICH light.

The compounds were analyzed after storage by HPLC and by visual inspection.

The results of the tests are reported in the following table H.

| product | condition | HPLC Sum of impurities | | | Appearance | | |
|---|---|---|---|---|---|---|---|
| | | 1 week | 4 weeks | 8 weeks | 1 week | 4 weeks | 8 weeks |
| Form II HCl salt | Reference | 5.04 | — | — | white | — | — |
| | 0.3 da ICH light | 7.42 | — | — | orange-brown | — | — |
| | 40° C./75% RH | 4.96 | 4.99 | 4.90 | slightly pink | pink | pink |
| | 50° C. | 4.96 | 5.00 | 4.90 | white | white | slightly pink |
| | RT/<5% RH | — | 5.10 | 4.98 | — | white | white |
| | RT/56% RH | — | 5.05 | 4.94 | — | slightly pink | slightly pink |
| | RT/75% RH | — | 5.03 | 4.97 | — | slightly pink | slightly pink |

The chemical stability study of the R425754 resulted in the following observations:

R425754 showed a sensitivity towards light, as the sum of impurities increases after storage in 0.3 da ICH light conditions.

Also a discoloration from white to or orange-brown is observed after storage in 0.3 da ICH light and from white to pink after storage in humid conditions RT/56% RH, RT/75% RH and 40° C./75% RH and elevated temperature 50° C.

The invention claimed is:

1. A process for preparing a compound of formula (XVIII) comprising a) reacting an intermediate of formula (VIII) with an intermediate of formula (XI) in the presence of a suitable solvent to produce an intermediate of formula (I),

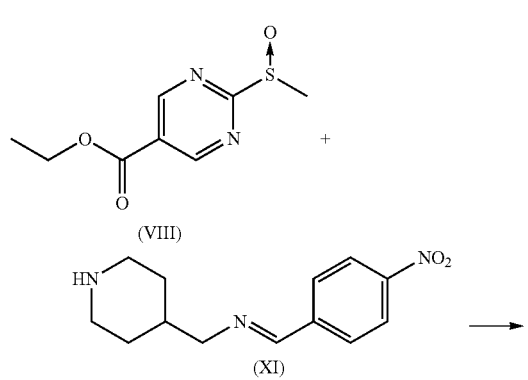

b) reacting the intermediate of formula (I) with an intermediate of formula (II) in a suitable solvent followed by reduction and salt formation to produce an intermediate of formula (XIII),

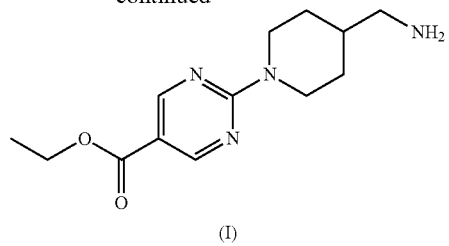

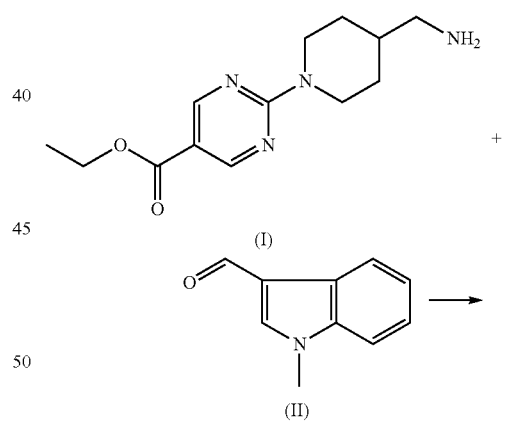

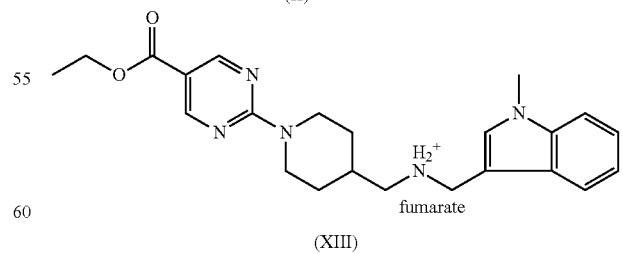

c) converting the intermediate of formula (XIII) by base neutralization, basic hydrolysis and acidification with hydrochloric acid to produce an intermediate of formula (XVII) and

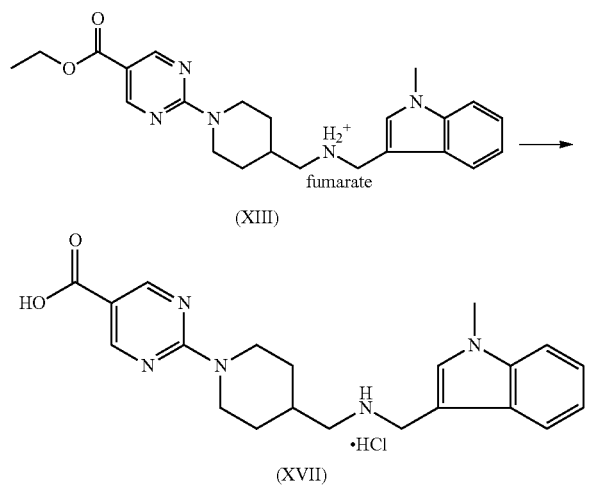

(XIII)

(XVII)

d) reacting the intermediate of formula (XVII) with O-(tetrahydro-2H-pyran-2-yl)-hydroxylamine, in the presence of an appropriate coupling reagent

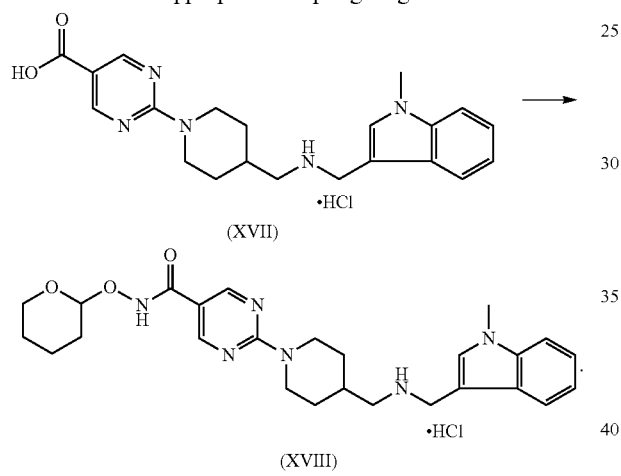

(XVII)

(XVIII)

2. The process of claim 1 wherein intermediate (XVII) comprises between 15 and 25 v/v % water.

3. A process for preparing a compound of formula (XI) comprising reacting an intermediate of formula (IX) with an intermediate of formula (X) in the presence of a suitable solvent

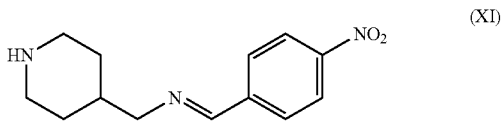 [SMILES: O=[N+]([O-])c1ccc(/C=N/CC2CCNCC2)cc1]

4. A compound of formula (XI)

(XI)

an N-oxide, addition salt or stereochemically isomeric form thereof.

\* \* \* \* \*